(12) United States Patent
Burke et al.

(10) Patent No.: US 9,539,122 B2
(45) Date of Patent: Jan. 10, 2017

(54) ANEURYSM TREATMENT DEVICE AND METHOD OF USE

(71) Applicant: MicroVention, Inc., Tustin, CA (US)

(72) Inventors: Thomas H. Burke, Grosse Point Wood, MI (US); Brian J. Cox, Laguna Niguel, CA (US); Matthew J. Fitz, Vista, CA (US); David Ferrera, Manhattan Beach, CA (US)

(73) Assignee: MicroVention, Inc., Tustin, CA (US)

( * ) Notice: Subject to any disclaimer, the term of this patent is extended or adjusted under 35 U.S.C. 154(b) by 16 days.

(21) Appl. No.: 14/223,939

(22) Filed: Mar. 24, 2014

(65) Prior Publication Data

US 2014/0288633 A1    Sep. 25, 2014

Related U.S. Application Data

(60) Division of application No. 10/892,884, filed on Jul. 16, 2004, now Pat. No. 8,715,312, which is a
(Continued)

(51) Int. Cl.
*A61F 2/82* (2013.01)
*A61B 17/12* (2006.01)
*A61F 2/06* (2013.01)

(52) U.S. Cl.
CPC ............. *A61F 2/82* (2013.01); *A61B 17/1219* (2013.01); *A61B 17/12022* (2013.01);
(Continued)

(58) Field of Classification Search
CPC ............... A61B 17/0057; A61B 17/12022; A61B 17/12118; A61B 17/12172; A61B 17/12177; A61B 17/1219; A61B 2002/823
See application file for complete search history.

(56) References Cited

U.S. PATENT DOCUMENTS 4,512,338 A    4/1985  Balko et al.
4,655,771 A    4/1987  Wallsten
(Continued)

FOREIGN PATENT DOCUMENTS

EP    1 266 631    12/2002
WO    WO 95/17859    7/1995
(Continued)

OTHER PUBLICATIONS

United States Patent and Trademark Office, Notice of Allowance mailed Dec. 24, 2013 in U.S. Appl. No. 10/892,884, 10 pages.
(Continued)

*Primary Examiner* — Julie A Szpira
(74) *Attorney, Agent, or Firm* — Inskeep IP Group, Inc.

(57) ABSTRACT

An apparatus for treating vascular aneurysms includes an occlusive support device comprised of one or more support members. The occlusive device has, an end cap member and an anchoring member. The end cap member is comprised of at least one of one or more of the support members. The end cap member has openings and the end cap member comprises a reactive material that is configured to hydrate upon delivery of the device and to reduce the size of said openings. The device is configured so that the occlusive members can be positioned in the blood vessel proximate the neck of a vascular aneurysm, the reactive material hydrates and increases the resistance to blood flow into the aneurysm, and the anchoring member anchors the device in the blood vessel without occluding flow through the blood vessel.

30 Claims, 15 Drawing Sheets

Related U.S. Application Data continuation-in-part of application No. 10/763,975, filed on Jan. 22, 2004, now Pat. No. 8,252,040, and a continuation-in-part of application No. 09/909,715, filed on Jul. 20, 2001, now Pat. No. 7,572,288.

(52) U.S. Cl.
CPC .. *A61B 17/12118* (2013.01); *A61B 17/12172* (2013.01); *A61B 17/12177* (2013.01); *A61B 17/12186* (2013.01); *A61B 2017/12054* (2013.01); *A61F 2002/065* (2013.01); *A61F 2002/823* (2013.01); *A61F 2250/0067* (2013.01)

(56) References Cited

U.S. PATENT DOCUMENTS

| | | | | |
|---|---|---|---|---|
| 4,733,665 | A | 3/1988 | Palmaz | |
| 4,941,870 | A | 7/1990 | Okada et al. | |
| 4,994,069 | A | 2/1991 | Ritchart et al. | |
| 5,015,253 | A | 5/1991 | MacGregor | |
| 5,162,430 | A | 11/1992 | Rhee et al. | |
| 5,226,911 | A | 7/1993 | Chee et al. | |
| 5,258,042 | A * | 11/1993 | Mehta | 600/36 |
| 5,389,106 | A | 2/1995 | Tower | |
| 5,410,016 | A | 4/1995 | Hubbell et al. | |
| 5,464,449 | A | 11/1995 | Ryan et al. | |
| 5,514,380 | A | 5/1996 | Song et al. | |
| 5,527,338 | A * | 6/1996 | Purdy | 606/200 |
| 5,536,274 | A | 7/1996 | Neuss | |
| 5,609,628 | A | 3/1997 | Keranen | |
| 5,609,629 | A | 3/1997 | Fearnot et al. | |
| 5,630,829 | A | 5/1997 | Lauterjung | |
| 5,674,241 | A | 10/1997 | Bley et al. | |
| 5,674,295 | A | 10/1997 | Ray et al. | |
| 5,741,325 | A | 4/1998 | Chaikof et al. | |
| 5,749,894 | A | 5/1998 | Engelson | |
| 5,750,585 | A | 5/1998 | Park et al. | |
| 5,769,882 | A | 6/1998 | Fogarty et al. | |
| 5,785,679 | A * | 7/1998 | Abolfathi et al. | 604/509 |
| 5,785,965 | A | 7/1998 | Pratt et al. | |
| 5,800,454 | A | 9/1998 | Jacobsen et al. | |
| 5,823,198 | A | 10/1998 | Jones et al. | |
| 5,843,089 | A | 12/1998 | Sahatjian et al. | |
| 5,911,717 | A | 6/1999 | Jacobsen et al. | |
| 5,911,731 | A | 6/1999 | Pham et al. | |
| 5,928,260 | A | 7/1999 | Chin et al. | |
| 5,935,148 | A | 8/1999 | Villar et al. | |
| 5,941,249 | A | 8/1999 | Maynard | |
| 5,951,599 | A | 9/1999 | McCrory | |
| 5,980,514 | A | 11/1999 | Kupiecki et al. | |
| 5,980,550 | A | 11/1999 | Eder et al. | |
| 5,980,554 | A | 11/1999 | Lenker et al. | |
| 5,990,237 | A | 11/1999 | Bentley et al. | |
| 6,015,431 | A | 1/2000 | Thornton et al. | |
| 6,036,720 | A | 3/2000 | Abrams et al. | |
| 6,063,111 | A | 5/2000 | Hieshima et al. | |
| 6,093,199 | A * | 7/2000 | Brown et al. | 606/200 |
| 6,113,629 | A | 9/2000 | Ken | |
| 6,120,847 | A | 9/2000 | Yang et al. | |
| 6,140,127 | A | 10/2000 | Sprague | |
| 6,152,144 | A * | 11/2000 | Lesh et al. | 128/898 |
| 6,165,193 | A * | 12/2000 | Greene et al. | 606/191 |
| 6,168,592 | B1 * | 1/2001 | Kupiecki et al. | 606/32 |
| 6,168,615 | B1 | 1/2001 | Ken et al. | |
| 6,176,240 | B1 | 1/2001 | Nikolchev et al. | |
| 6,177,095 | B1 | 1/2001 | Sawhney et al. | |
| 6,184,266 | B1 | 2/2001 | Ronan et al. | |
| 6,187,370 | B1 | 2/2001 | Dinh et al. | |
| 6,190,402 | B1 | 2/2001 | Horton et al. | |
| 6,193,708 | B1 | 2/2001 | Ken et al. | |
| 6,201,065 | B1 | 3/2001 | Pathak et al. | |
| 6,224,892 | B1 | 5/2001 | Searle | |
| 6,238,403 | B1 | 5/2001 | Greene, Jr. et al. | |
| 6,264,695 | B1 | 7/2001 | Stoy | |
| 6,309,367 | B1 * | 10/2001 | Boock | 602/1 |
| 6,554,849 | B1 * | 4/2003 | Jones et al. | 606/200 |
| 6,569,179 | B2 | 5/2003 | Teoh et al. | |
| 6,569,190 | B2 | 5/2003 | Whalen, II et al. | |
| 6,596,296 | B1 | 7/2003 | Nelson et al. | |
| 6,605,111 | B2 | 8/2003 | Bose et al. | |
| 6,605,294 | B2 | 8/2003 | Sawhney | |
| 6,613,073 | B1 | 9/2003 | White et al. | |
| 6,613,074 | B1 | 9/2003 | Mitelberg et al. | |
| 6,652,555 | B1 * | 11/2003 | VanTassel et al. | 606/200 |
| 6,663,607 | B2 * | 12/2003 | Slaikeu et al. | 604/265 |
| 6,802,851 | B2 * | 10/2004 | Jones et al. | 606/200 |
| 7,306,622 | B2 * | 12/2007 | Jones et al. | 623/1.15 |
| 2001/0000188 | A1 | 4/2001 | Lenker et al. | |
| 2002/0013618 | A1 * | 1/2002 | Marotta | A61F 2/82 623/1.15 |
| 2002/0026228 | A1 | 2/2002 | Schauerte | |
| 2002/0123789 | A1 | 9/2002 | Francis et al. | |
| 2003/0004531 | A1 | 1/2003 | Jones et al. | |
| 2003/0055451 | A1 | 3/2003 | Jones et al. | |
| 2003/0120300 | A1 | 6/2003 | Porter | |
| 2003/0139802 | A1 | 7/2003 | Wulfman et al. | |
| 2003/0171739 | A1 | 9/2003 | Murphy et al. | |
| 2004/0111112 | A1 | 6/2004 | Hoffmann | |
| 2004/0172056 | A1 | 9/2004 | Guterman et al. | |

FOREIGN PATENT DOCUMENTS

| | | |
|---|---|---|
| WO | WO 98/50102 | 11/1998 |
| WO | WO 99/02092 | 1/1999 |
| WO | WO 99/05977 | 2/1999 |
| WO | WO 99/59479 | 11/1999 |
| WO | WO 99/62429 | 12/1999 |
| WO | WO 99/62432 | 12/1999 |
| WO | WO 99/65397 | 12/1999 |
| WO | WO 00/04845 | 2/2000 |
| WO | WO 00/07524 | 2/2000 |
| WO | WO 00/13593 | 3/2000 |
| WO | WO 00/18321 | 4/2000 |
| WO | WO 00/32112 | 6/2000 |
| WO | WO 00/44306 | 8/2000 |
| WO | WO 00/56247 | 9/2000 |
| WO | WO 00/57818 | 10/2000 |
| WO | WO 00/74577 | 12/2000 |
| WO | WO 01/01890 | 1/2001 |
| WO | WO 01/03607 | 1/2001 |
| WO | WO 01/37892 | 5/2001 |
| WO | WO 01/41676 | 6/2001 |
| WO | WO 02/05731 | 1/2002 |
| WO | WO 02/080782 | 10/2002 |
| WO | WO 02/080782 A1 | 10/2002 |
| WO | WO 02/087472 | 11/2002 |

OTHER PUBLICATIONS

United States Patent and Trademark Office, Office Action mailed Jul. 17, 2013 in U.S. Appl. No. 10/892,884, 10 pages.
United States Patent and Trademark Office, Final Office Action mailed Jun. 21, 2012 in U.S. Appl. No. 10/892,883, 10 pages.
United States Patent and Trademark Office, Office Action mailed Dec. 27, 2011 in U.S. Appl. No. 10/892,884, 9 pages.
United States Patent and Trademark Office, Final Office Action mailed Jul. 8, 2011 in U.S. Appl. No. 10/892,884, 8 pages.
United States Patent and Trademark Office, Office Action mailed Jan. 24, 2011 in U.S. Appl. No. 10/892,884, 8 pages.
United States Patent and Trademark Office, Examiner Interview Summary mailed Jul. 21, 2010 in U.S. Appl. No. 10/892,884, 3 pages.
United States Patent and Trademark Office, Final Office Action mailed Mar. 8, 2010 in U.S. Appl. No. 10/892,884, 9 pages.
United States Patent and Trademark Office, Office Action mailed Jul. 22, 2009 in U.S. Appl. No. 10/892,884, 7 pages.
United States Patent and Trademark Office, Final Office Action mailed Jan. 27, 2009 in U.S. Appl. No. 10/892,884, 8 pages.
United States Patent and Trademark Office, Office Action mailed Aug. 7, 2008 in U.S. Appl. No. 10/892,884, 18 pages.

(56) References Cited

OTHER PUBLICATIONS

Lownie, *Endovascular Therapy of a Large Vertebral Artery Aneurysm Using Stent and Coils*, Canadian Journal of Neurological Sciences vol. 27, No. 2, pp. 162-165, May 2000.
Whitelock, *Perlecan Coating of Vascular Grafts Enhances Endothelial Cell Growth*, Society for Biomaterials, p. 953, 2000.
Klee, *Bioactive Coating of Platinum Surfaces for Embolization Coils*, Society for Biomaterials, p. 215, 2000.
Raymond, *Fibrinogen and Vascular Smooth Muscle Cell Grafts Promote Healing of Experimental Aneurysms Treated by Embolization*, httD://www.strokeaha.ora. p. 1657-1664,1999.
Kalra, *Transcatheter Closure of Ventricular Septal Defect Using Detachable Steel Coil*, Heart 82: 395-396, 1999.
Wakhloo, *Stents for Intracranial Aneurysms: The Beginning of a New Endovascular Era?*, Neurosurgery, vol. 43, No. 2, pp. 377-379, Aug. 1998.
Vinuela, *Guglielmi Detachable Coil Embolization of Acute Intracranial Aneurysm: Perioperative Anatomical and Clinical Outcome in 403 Patients*, J. Neurosurg. 86:475-482, 1997.
Post, *Experimental Nonsurgical Transcervical Sterilization with a Custom-Designed Platinum Microcoli*, Journal of Vascular and Interventional Radiology vol. 8:113-118, Jan./Feb. 1997.
Massoud, *Endovascular Treatment of Fusiform Aneurysms with Stents and Coils: Technical Feasibility in a Swine Model*, AJNR 16:2953-1963, Nov. 1995.
Dawson, *Treatment of Experimental Aneurysms Using Collagen-Coated Microcoils*, Neurosurgery 36:133-140, 1995.
Geremia, et al. *Embolization of Experimentally Created Aneurysms with Intravascular Stent Devices*, AJNR 15:1223-1231, Aug. 1994.
Turjman, *Combined Stent Implantation and Endosaccular Coil Placement for Treatment of Experiemental Wide-Necked Aneurysms: A Feasibility Study in Swine*, AJNR: 15:1087-1990, Jun. 1994.
Szikora, *Combined Use of Stents and Coils to Treat Experiemental Wide-Necked Carotid Aneurysms: Preliminary Results*, AJNR 15:1091-1102, Jun. 1994.
Ahuja, *Platinum Coil Coatings to Increase Thrombogenicity: A Preliminary Study in Rabbits*, AJNR 14:794-798, Jul.-Aug. 1993.
Weber, J., M.D., *Techniques and Results of Therapeutic Catheter Embolization of Congenital Vascular Defects*, Int. Angiol. vol. 9:214-223, 1990.
Hoepp, *Transcatheter Closure of Atrial-Septal Defects and Patnet Foramen Ovale in Adults: Optimal Anatomic Adaptation of Occlusion Device*, American Heart Journal, vol. 138, No. 5, Part 1, pp. 941-949.

\* cited by examiner

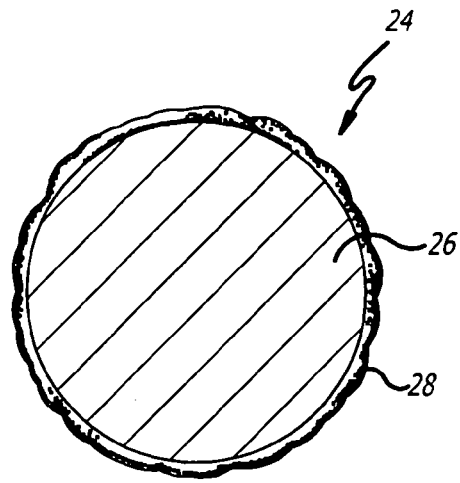
FIG. 4
FIG. 5a
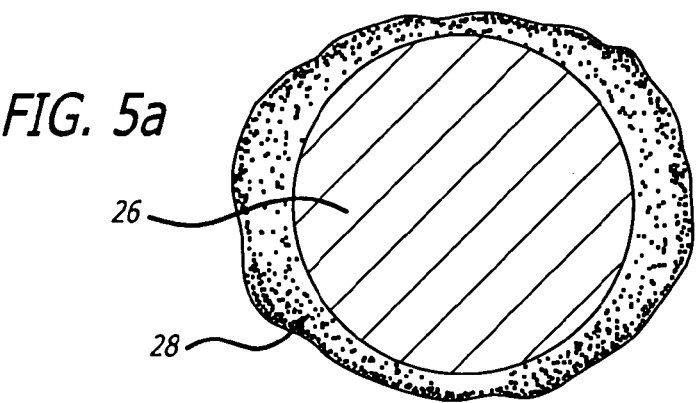
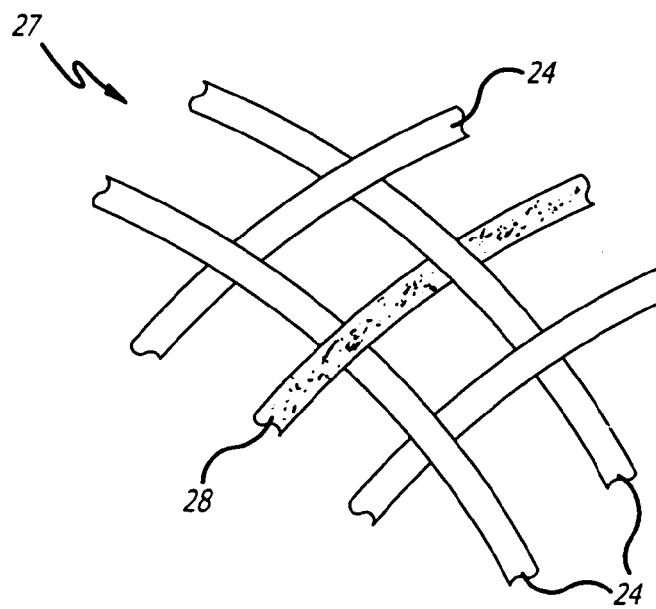
FIG. 5b

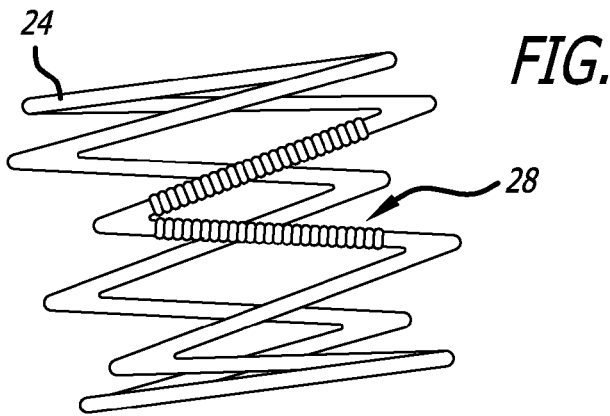
FIG. 5D
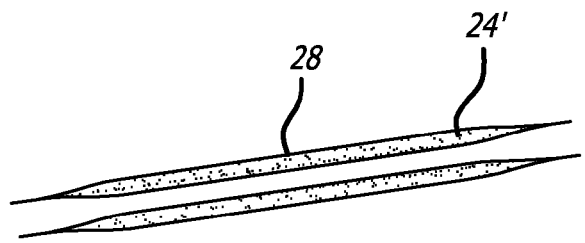
FIG. 5F
FIG. 5E
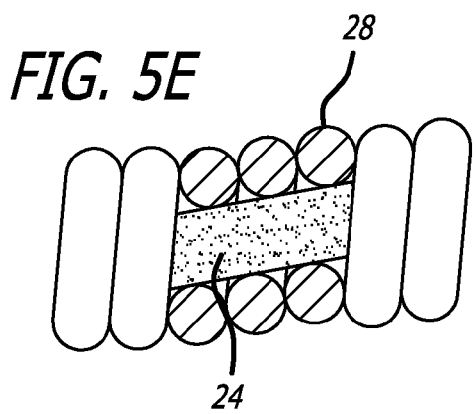
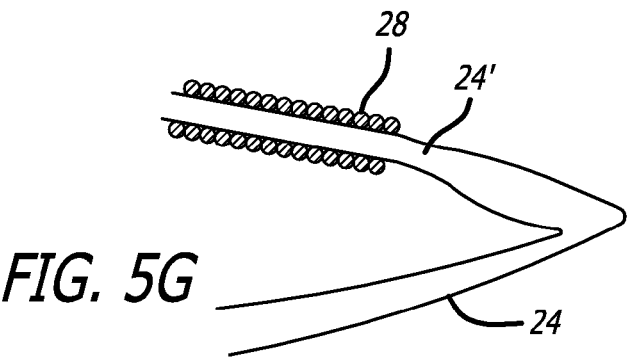
FIG. 5G

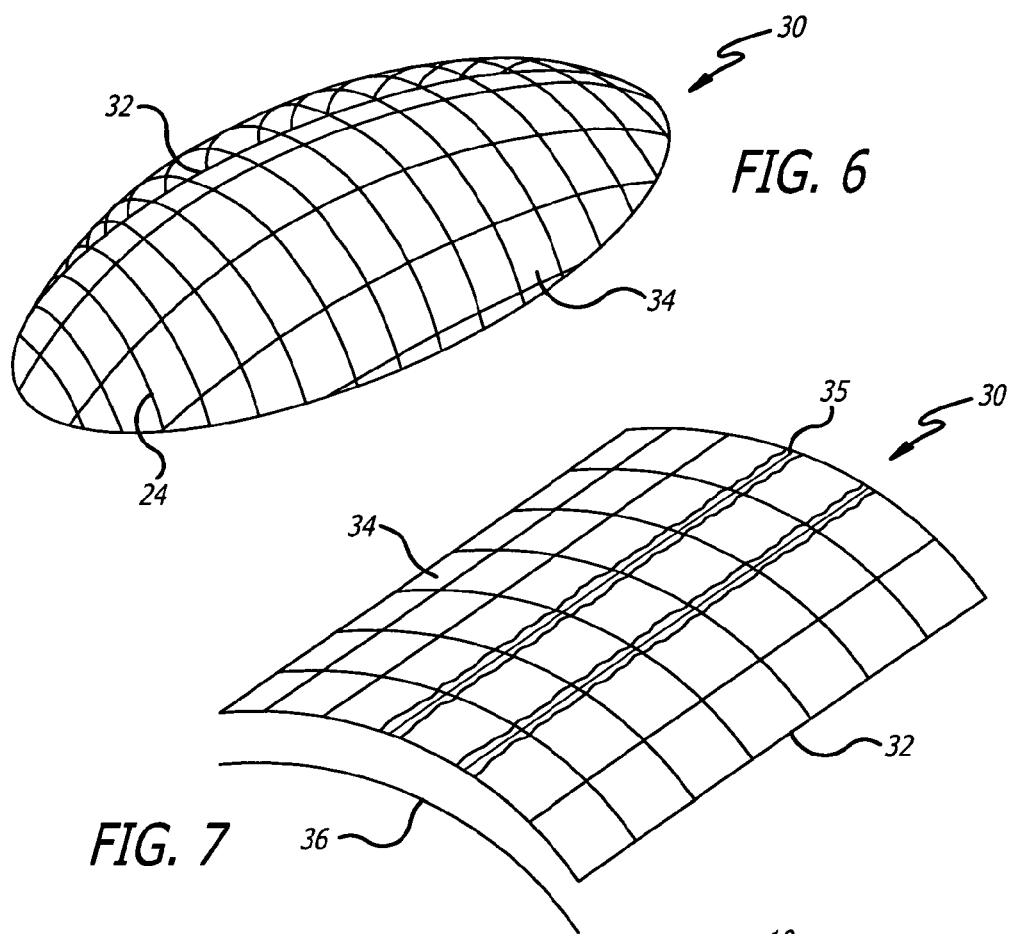
FIG. 6
FIG. 7
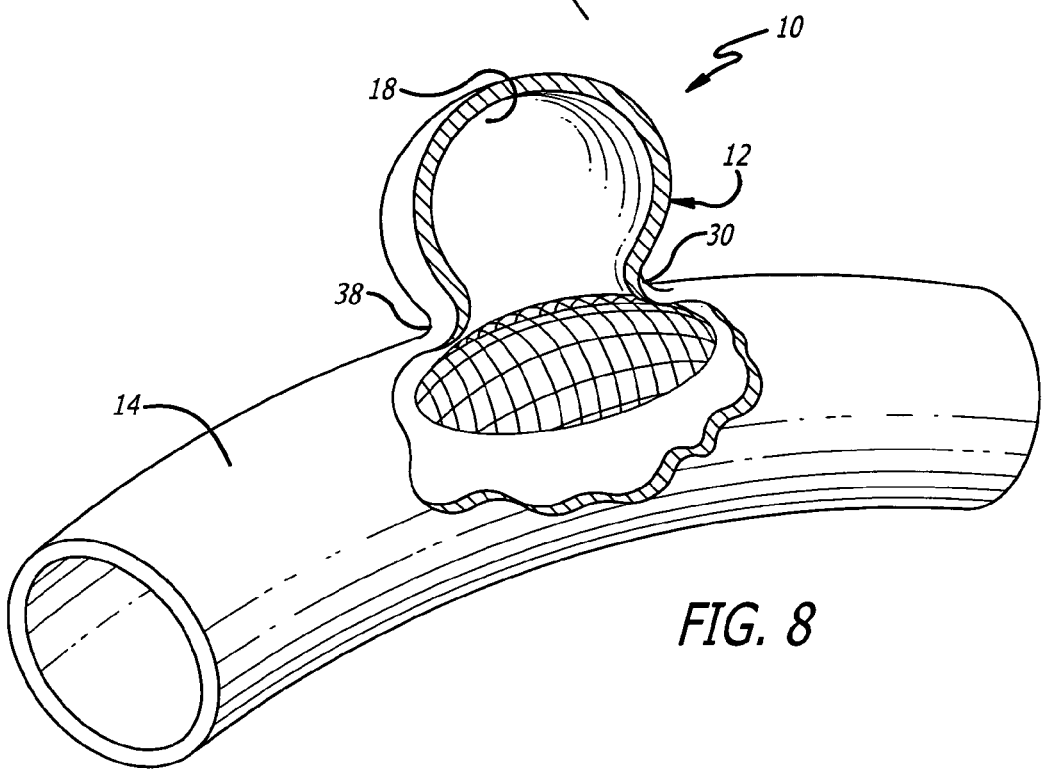
FIG. 8

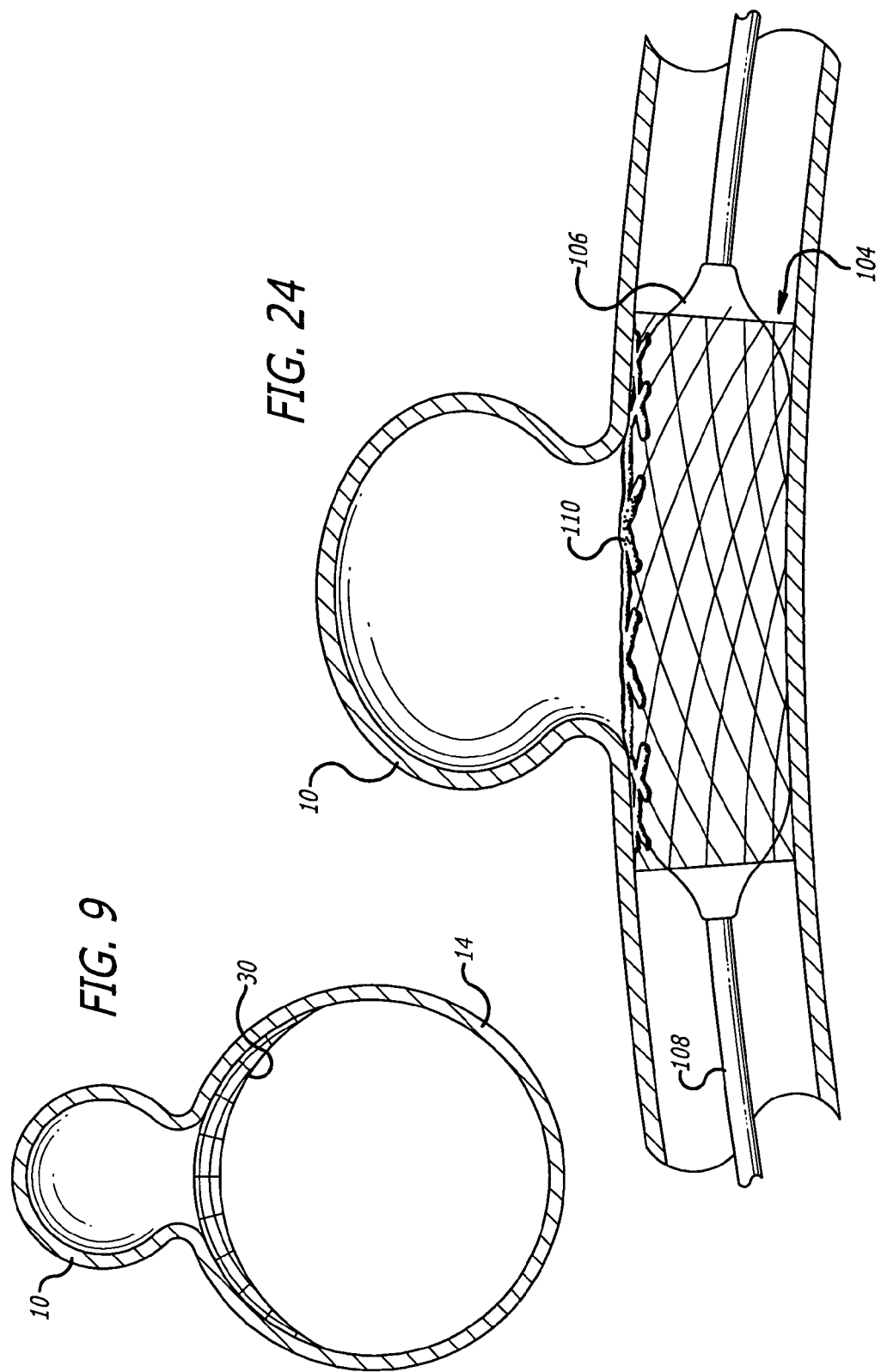

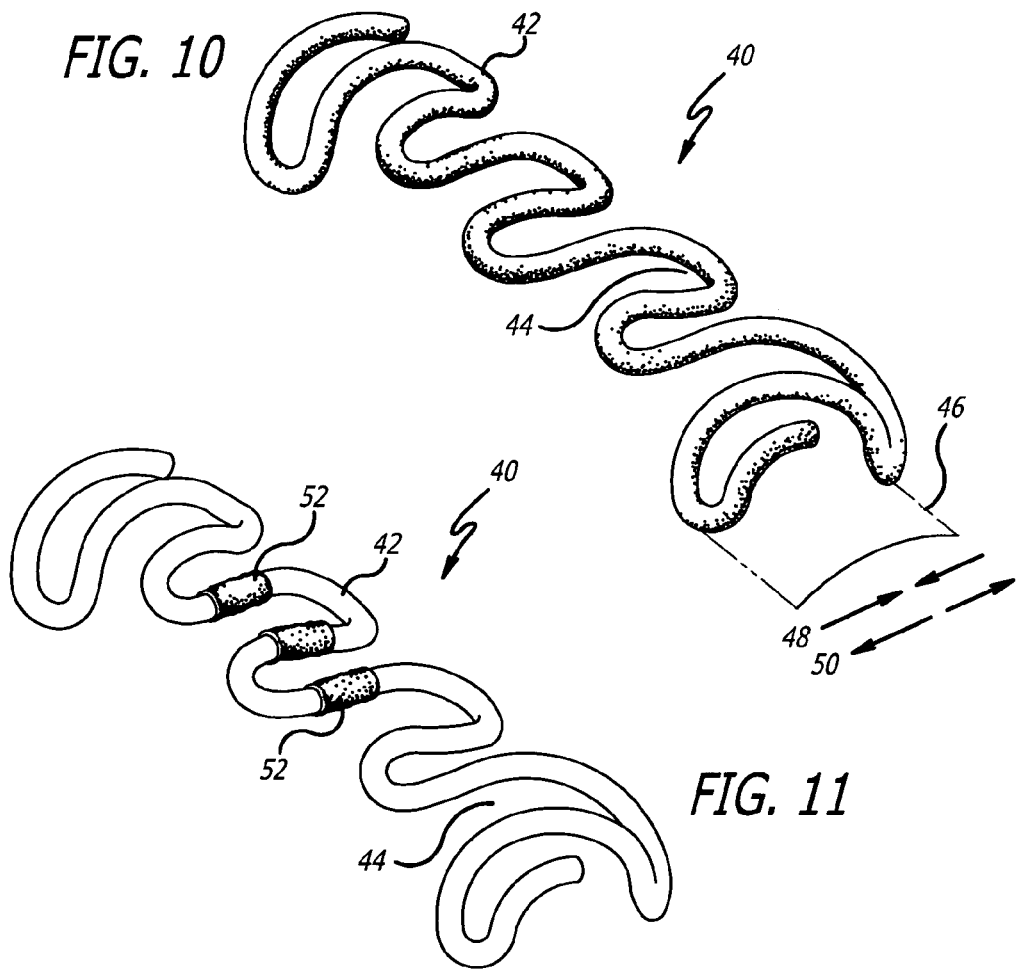
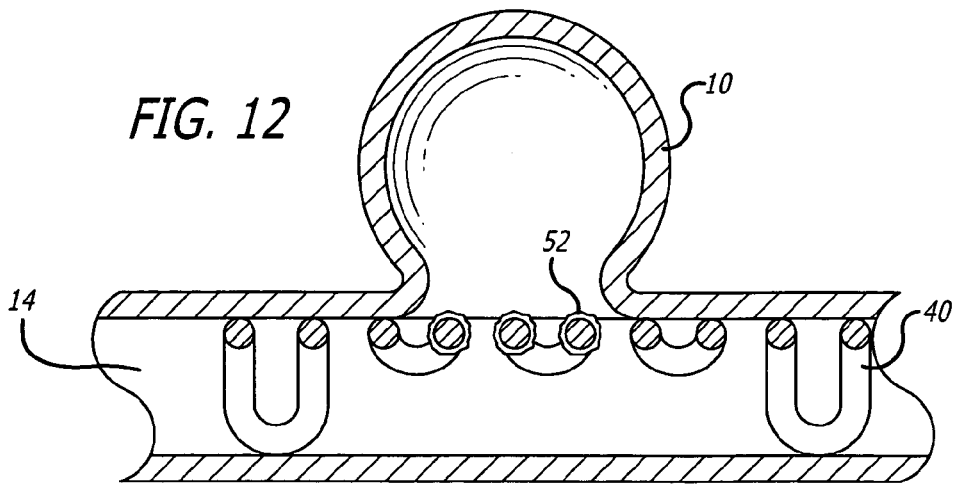

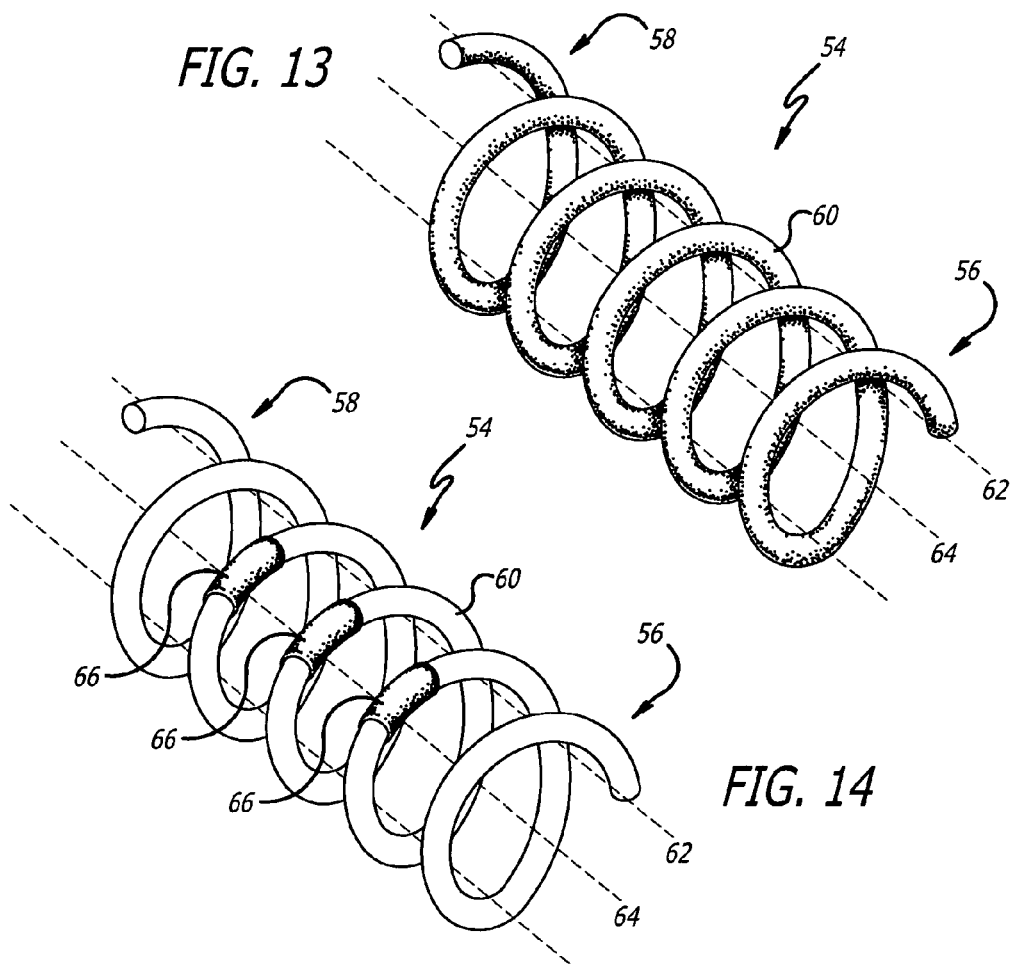
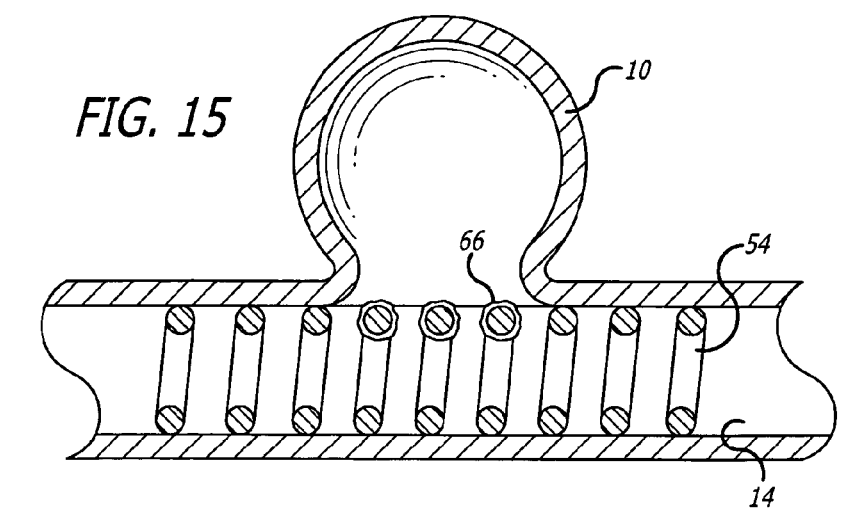

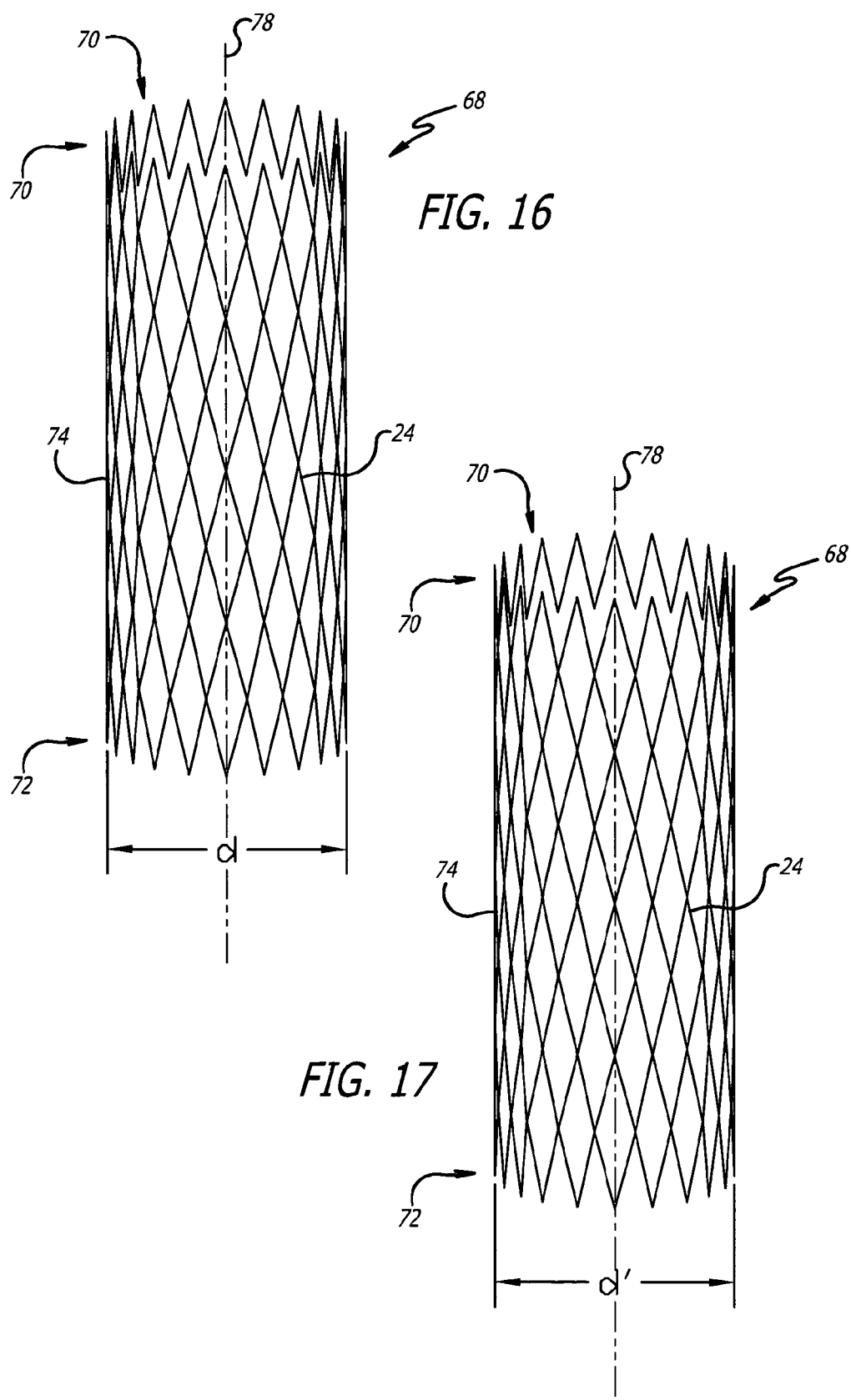

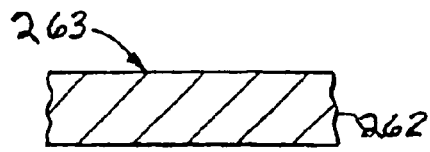
FIG. 25a
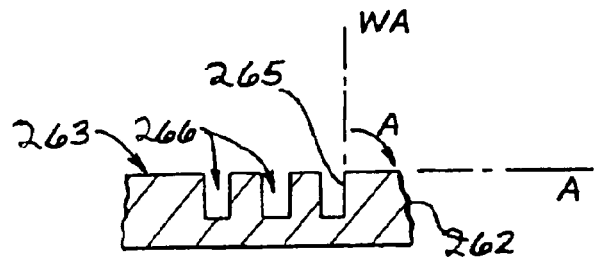
FIG. 25b
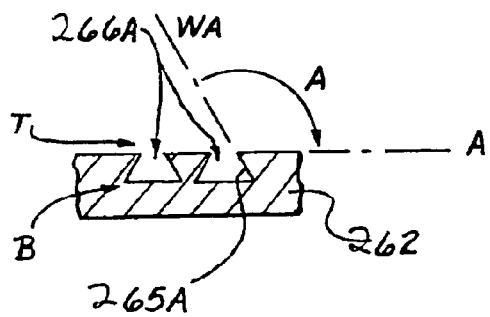
FIG. 25b (ALT)
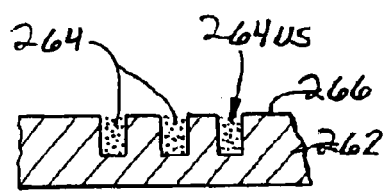
FIG. 25C
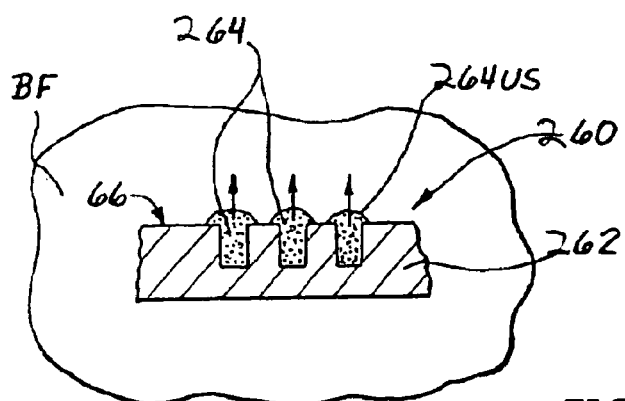
FIG. 25D

ANEURYSM TREATMENT DEVICE AND METHOD OF USE

CROSS REFERENCE TO RELATED APPLICATIONS

The present application is a divisional of U.S. patent application Ser. No. 10/892,884 filed Jul. 16, 2004 entitled "Aneurysm Treatment Device And Method Of Use", which is a continuation-in-part of U.S. patent application Ser. No. 10/763,975, entitled "Aneurysm Treatment Device and Method of Use," filed on Jan. 22, 2004 (now U.S. Pat. No. 8,252,040 issued Aug. 28, 2012), and is also a continuation-in-part of U.S. patent application Ser. No. 09/909,715, entitled "Aneurysm Closure Device and Method of Use," filed on Jul. 20, 2001 (now U.S. Pat. No. 7,572,288 issued Aug. 11, 2009), all of which are hereby incorporated by reference in their entireties. The entire contents of U.S. patent application Ser. No. 09/804,935, entitled "Hydrogels That Undergo Volumetric Expansion In Response To Changes In Their Environment And Their Methods Of Manufacture And Use," filed on Mar. 31, 2001, naming Gregory M. Cruise and Michael J. Constant as co-inventors (now U.S. Pat. No. 6,878,384 issued Apr. 12, 2005), is hereby incorporated in its entirety by this reference.

BACKGROUND

Generally, the mammalian circulatory system is comprised of a heart, which acts as a pump, and a system of blood vessels which transport the blood to various points in the body. Due to the force exerted by the flowing blood on the blood vessel the blood vessels may develop a variety of vascular disabilities or dysfunctions. One common vascular dysfunction known as an aneurysm results from the abnormal widening of the blood vessel. Typically, vascular aneurysms are formed as a result of the weakening of the wall of a blood vessel and subsequent ballooning of the vessel wall. As shown in FIG. 1, the aneurysm 10 often comprises a narrow neck portion 12 which is in communication with the blood vessel 14 and a dome portion 16 in communication with the neck portion 12. As shown in FIG. 1 the neck portion 12 and the dome portion 16 form a cavity 18. Aneurysms have been known to form in a plurality of location though the body, including, for example, the brain, the abdomen, and throughout the circulatory system.

In response, several surgical techniques for treating aneurysms have been developed. Initially, an aneurysmectomy was required to repair the dysfunctional tissue. The aneurysmectomy procedure requires the surgeon to gain access to the aneurysm, excise the aneurysm, and replace the void with a prosthetic graft. Because this is a major surgical undertaking, the mortality rate of the procedure is relatively high. Commonly, the aneurysmectomy procedure is unavailable to patients with severe coronary or cerebral arteriosclerosis, severe restrictive pulmonary disease, and significant renal disease or other complicating factors. An alternate method of treating cerebral aneurysms called 'microsurgical clipping' requires the placement of a metallic clip across the neck of the aneurysm, thereby excluding the aneurysm from the blood flow.

In response to the shortcomings of the aneurysmectomy and the microsurgical clipping procedures, less invasive methods of treatment have been developed. Commonly, these procedures require the formation of an artificial vaso-occlusion, which is obtained by implanting a number of devices or suitable materials into the cavity 18 of the aneurysm, thereby resulting in a decrease in the flow of blood into the aneurysm. The reduced flow results in hemostasis and the formation of a clot. Generally, this procedure requires the surgeon to advance a micro-catheter to a location inside the aneurysm and deposit a biologically-compatible vaso-occlusive material or device therein. Typical vaso-occlusive devices and materials include platinum microcoils, hog hair, microfibrillar collagen, various polymeric agents, material suspensions, and other space filling materials.

FIG. 2 shows an aneurysm 10 formed on a blood vessel 14, the aneurysm 10 having a vaso-occlusive device 20 positioned within the aneurysm dome 18. A disadvantage of filling an aneurysm with devices is that the vaso-occlusive mass may impinge on nerves or other biological structures, thereby resulting in adverse biological symptoms. For example, the impingement of the vaso-occlusive device 20 on structures or nerves within the brain, commonly known as 'mass effect', may result in adverse neurological symptoms. Another problem associated with vaso-occlusive devices is maintaining the device within the aneurysm. Blood flow through an otherwise functional blood vessel may be compromised should the device migrate from the aneurysm during or following implantation, thereby possibly resulting in a vascular embolism. Yet another problem associated with certain vaso-occlusive devices, such as coils, is that the coils may migrate out of aneurysms having wide necks into the parent vessel. Thus, only aneurysms having certain dome to neck ratios can be treated in this fashion.

An alternate method of repairing an aneurysm has been developed which requires the implantation of a mechanical support device within the blood vessel near the neck portion of the aneurysm. Generally, these mechanical support devices, commonly referred to as "stents", comprise deployable mechanical support structures capable of delivery to a situs within the blood vessel through catheters. In addition to providing mechanical support to the dysfunctional vessel wall, the stent may include a mechanical structure which seeks to restrict the blood flow though the portion of the blood vessel proximate the aneurysm, thereby reducing or eliminating the aneurysm. The stent may also be useful in preventing coils from migrating out of the aneurysm. Exemplary mechanical structures capable of restricting blood flow to an aneurysm include meshes or fenestrated structures which are positioned near an aneurysm 10 and restrict the flow of blood thereto.

FIG. 3 shows a stent 22 positioned in a blood vessel 14 proximal to an aneurysm 10. While a stent may provide adequate mechanical support to the blood vessel, these devices have demonstrated limited effectiveness in limiting blood flow to the aneurysm. As such, the aneurysm typically remains intact and may increase in size. In response, stents may be covered with various coatings designed to limit blood flow to the aneurysm. These coatings typically include biologically compatible polymers, films, and fabrics. However, the application of these coatings to the stents increases the cross-sectional diameter of the device, thereby resulting in a high profile stent-graft. As a result, the blood flow through the blood vessel is reduced by the presence of a high profile stent-graft. In addition, device profile is a significant problem for the treatment of cerebral aneurysms due to the small size of the cerebral blood vessels, therefore requiring the device to be deliverable to the aneurysm through a micro-catheter. As such, high profile stent-grafts are typically not used in the treatment of cerebral aneurysms.

There are additional limitations in the use of conventional stents to treat cerebral aneurysms. Since stents have a cylindrical shape, it is less useful for treating an aneurysm that is formed at a bifurcation of an artery or in arteries with complex geometries. Also, self-expanding stents can be difficult to deliver because, when collapsed, they will exert a radial force on the delivery sheath that is proportional to its length. The user must overcome this radial force to deliver the stent. As the delivery sheath is retracted against this force, energy is stored in the delivery system and released as the stent is deployed, causing considerable movement in the system during deployment. This issue is usually addressed by utilizing a stent that is longer than the aneurysm neck so that accuracy of delivery is less crucial. However, this also tends to increase the radial force holding the stent in the delivery system which only exacerbates the problem of stored energy, thus creating a viscous cycle. Balloon expandable stents can mitigate this problem, but the balloon makes the device stiffer and more difficult to navigate tortuous cerebral anatomy.

Thus, there is presently an ongoing need for a device and method for effectively treating aneurysms without significantly affecting blood flow through the blood vessel.

There is also an ongoing need for a device that can be used in conjunction with or in lieu of coils that can occlude an aneurysm without adversely affecting blood flow through the vessel.

SUMMARY

The aneurysm treatment devices of the present application effectively occlude or inhibits blood flow to an aneurysm without substantially impairing blood flow through the blood vessel. In addition, the aneurysm treatment devices of the present application are capable of being applied to a variety of aneurysms formed on blood vessels throughout the body.

In one embodiment, the aneurysm treatment device of the present invention comprises at least one support member and reactive material selectively applied to the support member. The at least one support member, which has at least a first surface capable of receiving the reactive material, provides a substrate for receiving the reactive material. Alternatively, the at least one support member may also provide support to weakened vascular tissue. The reactive material has a non-reacted state and a reacted state. In a reacted stated the reactive material, as selectively applied to the at least one support member, is capable of increasing the resistance to the flow of blood to the aneurysm. In an alternate embodiment, the at least one support member may be manufactured from or otherwise incorporate reactive material therein. The device is preferably controllably released from an elongate delivery apparatus. The release mechanism may be any of the vaso-occlusive device and stent detachment means known in the art including but not limited to mechanical, electrolytic, electro-mechanical, thermal, hydraulic, and shape-memory means.

In an alternate embodiment, the present invention is directed to a vascular patch comprising a radially and axially flexible patch body formed by a plurality of interlocking support members. The interlocking support members, which are capable of supporting vascular tissue, form a plurality of fenestrations. A reactive material capable of increasing the resistance to the flow of blood to an aneurysm is selectively applied to, woven into, integral to, or otherwise incorporated into the interlocking support member. For example, the interlocking member may be manufactured from fibrous or formed reactive material In yet another embodiment, the present invention is directed to a coiled bridge device comprising radially and axially flexible resilient sinusoidal body member which defines a plurality of openings. The sinusoidal body member has a first radius of curvature R and a second radius of curvature R', wherein R' is larger than R. The sinusoidal body member is formed by at least one support member and has a reactive material capable of increasing the resistance to the flow of blood to an aneurysm, selectively applied thereto.

In another embodiment, the present invention is directed to a helical stent having a radially and axially flexible cylindrical body member positioned between a first end and a second end. The cylindrical body member, which is formed by at least one support member capable of supporting vascular tissue, defines an internal lumen which is in communication with the first and second ends. A reactive material capable of increasing the resistance to the flow of blood to an aneurysm is selectively applied to the at least one support member.

In yet another embodiment, the present invention is directed to a helical stent having a radially and axially flexible cylindrical body member positioned between a first end and a second end. The cylindrical body member, which is formed by at least one support member capable of supporting vascular tissue, defines an internal lumen which is in communication with the first and second ends. A reactive material capable of increasing the resistance to the flow of blood to an aneurysm is selectively applied to the at least one support member.

In another embodiment, the present invention is directed to a reticulated expandable stent comprising radially and axially flexible cylindrical body member positioned between a first end and a second end. The cylindrical body member, which is formed by at least one support member capable of supporting vascular tissue, defines an internal lumen which is in communication with the first and second ends. A reactive material capable of increasing the resistance to the flow of blood to an aneurysm is selectively applied to the at least one support member.

In still another embodiment, the present invention is directed to a bifurcated vascular support device comprising a bifurcated body member positioned between a first end, a second end, and a third end. The bifurcated body member further defines an internal lumen which communicates with the first, second, and third ends. The bifurcated body member is formed by at least one support member capable of supporting vascular tissue. A reactive material capable of increasing the resistance to the flow of blood to an aneurysm is selectively applied to the at least one support member.

In another embodiment, the present invention is directed to an intra-aneurysmal bridge device comprising a flexible bridge body in communication with at least two engagement members. The at least two engagement members cooperatively form a joint. A reactive material capable of increasing the resistance to the flow of blood to an aneurysm is selectively applied to the at least two engagement members.

The present invention also discloses a novel method of treating a vascular aneurysm. More particularly, the novel method of treating vascular aneurysms comprises the steps of providing a device for treating vascular aneurysms having a reactive material applied thereto, delivering the device to a vascular aneurysm, supporting the tissue near the aneurysm with the device, and allowing the reactive material to react thereby permitting the flow of blood through the blood vessel while increasing the resistance to the flow of blood to the aneurysm In yet another embodiment, the present application discloses an apparatus for treating vascular aneurysms and includes a radially expandable structure formed from at least one support member and defining a plurality of openings, and at least one reactive material selectively applied to a portion of the at least one support member. The reactive material is configured to assume a reacted state which increases the resistance to the flow of blood to an aneurysm.

In another embodiment, the present application discloses an apparatus for treating aneurysms and includes at least one support member defining an expandable support body, at least one reactive material selectively applied to at least one support member and having a non-reacted state and a reacted state. The support member has a diameter D in a non-reacted state and a diameter D' in a reacted state, wherein diameter D' is larger than diameter D.

In another embodiment, the present application is directed to an apparatus for treating vascular aneurysms and includes an occlusive support defined by one or more support members and having a first end and a second end and a lumen formed therein, one or more fenestrations formed on the occlusive support and configured to permit blood to flow therethrough, an end cap secured to the second end and configured to restrict the flow of blood therethrough. The end cap may be configured to have a relatively short extension along the longitudinal axis of the device. In one embodiment the extension of the end cap is less than two times the end cap diameter. In another embodiment the extension of the end cap along the longitudinal axis of the device is less than the end cap diameter.

In another embodiment, the present application is directed to an apparatus for treating vascular aneurysm and includes an occlusive support device having a first end portion and a second end portion, a mesh member at said first end portion of the occlusive support device, an anchoring member at the said second end portion, and a plurality of elongated members connecting the mesh member to the anchoring member.

The present application further discloses a method of treating a vascular aneurysm and includes providing a device having a reactive material selectively applied to at least one support member, delivering the device to a position in a blood vessel proximate a vascular aneurysm, expanding the device to approximately a diameter of a blood vessel, and activating the reactive material disposed on the device to reduce the flow of blood into the aneurysm.

In another embodiment, the present application discloses a method of treating a vascular aneurysm and includes providing a device having at least one support member and an end cap secured to the support member, delivering the device to a position in a blood vessel proximate a vascular aneurysm, expanding the device to approximately the diameter of the blood vessel, and reducing a flow of blood to the aneurysm with the end cap while permitting blood flow through the blood vessel.

In another embodiment, the present application discloses a method of treating a vascular aneurysm and includes providing a device having at least one support member and an end cap secured to the support member, delivering the device to a position in a blood vessel proximate a vascular aneurysm, expanding the device to approximately the diameter of the blood vessel, delivering a catheter through the blood vessel to a position proximate to the vascular aneurysm, inserting a space occupying material into the aneurysm, and maintaining the space occupying material within the aneurysm with the end cap to reduce the flow of blood into the aneurysm.

In another embodiment, the present application discloses a method of treating a vascular aneurysm and includes providing a device having at least one support member and an end cap secured to the support member, the end cap having a reactive material disposed thereon, delivering the device to a position in the blood vessel proximate a vascular aneurysm, expanding the device to approximately a diameter of a blood vessel, delivering a catheter through the blood vessel to a position proximate to the vascular aneurysm, inserting a space occupying material into the aneurysm, and activating the reactive material to maintain the space occupying material within the aneurysm with the end cap to reduce the flow of blood into the aneurysm.

In yet another embodiment, the present application discloses a method of treating a vascular aneurysm and includes providing a device having an occlusive member at a first end portion and an anchoring member at a second end portion, and a plurality of elongated members connecting the occlusive member to the anchoring member, positioning the device in the blood vessel so that the occlusive member is proximate the neck of a vascular aneurysm to reduce the flow of blood into the aneurysm, deploying the elongated members and then the deploying anchoring member in the blood vessel so that that anchoring member anchors the device in the blood vessel without occluding flow through the blood vessel.

Other objects and further features of the aneurysm treatment device of the present application will become apparent from the following detailed description when read in conjunction with the attached drawings.

BRIEF DESCRIPTION OF THE DRAWINGS

The aneurysm treatment device of the present application will be explained in more detail by way of the accompanying drawings, wherein:

FIG. 4 shows a sectional view of a support member of an aneurysm treatment device having non-reacted reactive material disposed thereon;

FIG. 5a shows a sectional view of a support member of an aneurysm treatment device having reacted reactive material disposed thereon;

FIG. 5b shows a perspective view of an embodiment of an aneurysm treatment device comprising a structure having reactive material interwoven therein in a non-reacted state;

FIG. 5d shows a perspective view of an embodiment of an aneurysm treatment device having a reactive material strand wrapped around a support member;

FIG. 5e shows a cross-sectional view of an embodiment of an aneurysm treatment device having a reactive material strand wrapped around a support member;

FIG. 5f shows a sectional view of an embodiment of an aneurysm treatment device having a support member with a variable tangential width and a reactive material strand applied thereto;

FIG. 5g shows another sectional view of an embodiment of an aneurysm treatment device having a support member with a variable tangential width and a reactive material strand applied thereto;

FIG. 6 shows a perspective view of an embodiment of an aneurysm treatment device comprising a vascular patch device useful in restricting the flow of blood to a vascular aneurysm;

FIG. 7 shows another perspective view of an embodiment of an aneurysm treatment device comprising a vascular patch device useful in restricting the flow of blood to a vascular aneurysm;

FIG. 8 shows a perspective view of an embodiment of an aneurysm treatment device positioned within a blood vessel proximate a vascular aneurysm;

FIG. 9 shows a cross-sectional view of an embodiment of an aneurysm treatment device positioned within a blood vessel proximate a vascular aneurysm;

FIG. 10 shows a perspective view of an embodiment of an aneurysm treatment device comprising a coiled bridge device useful in restricting the flow of blood to a vascular aneurysm;

FIG. 11 shows a perspective view of another embodiment of an aneurysm treatment device comprising a coiled bridge device useful in restricting the flow of blood to a vascular aneurysm;

FIG. 12 shows a cross-sectional view of an embodiment of the aneurysm treatment device of FIG. 11 positioned within a blood vessel proximate a vascular aneurysm;

FIG. 13 shows a perspective view of an embodiment of an aneurysm treatment device comprising a helical stent device useful in restricting the flow of blood to a vascular aneurysm;

FIG. 14 shows a perspective view of another embodiment of an aneurysm treatment device comprising a helical stent device useful in restricting the flow of blood to a vascular aneurysm;

FIG. 15 shows a cross-sectional view of the embodiment of the aneurysm treatment device shown in FIG. 14 positioned within a blood vessel proximate a vascular aneurysm;

FIG. 16 shows a perspective view of another embodiment of an aneurysm treatment device comprising a reticulated stent device useful in restricting the flow of blood to a vascular aneurysm;

FIG. 17 shows a perspective view of another embodiment of the reticulated stent device useful in restricting the flow of blood to a vascular aneurysm;

FIG. 24 shows a partial longitudinal sectional view of a solid, elongate device which has a reactive material disposed thereon in accordance with the present invention;

FIGS. 25a-25d show, in step by step fashion, a method for manufacturing a device having a reactive material disposed thereon;

FIG. 28 shows a perspective view of an embodiment of an aneurysm treatment device positioned on an expandable balloon micro-catheter within a blood vessel.

DETAILED DESCRIPTION

Disclosed herein is a detailed description of various illustrated embodiments of the invention. This description is not to be taken in a limiting sense, but is made merely for the purpose of illustrating the general principles of the invention. The section titles and overall organization of the present detailed description are for the purpose of convenience only and are not intended to limit the present invention.

The aneurysm treatment devices of the present application are generally used to restrict the ability of blood flowing through a blood vessel from entering an aneurysm formed thereon or to otherwise limit the amount of blood within an aneurysm. The devices disclosed herein may be applied to a blood vessel in a variety of ways, including, without limitation, conventional surgical techniques and minimally invasive surgical techniques utilizing catheters of various sizes, balloon catheters, micro-catheters, and other ways generally known in the art of minimally invasive surgery. The aneurysm treatment devices disclosed herein may be used to repair a variety of aneurysms at various locations throughout the body. For example, in one embodiment these devices may be used in procedures to repair or otherwise treat cerebrovascular aneurysms.

The devices and methods of the present application have particular compatibility with the materials and methods of manufacture and use disclosed in co-pending U.S. patent application Ser. No. 09/804,935 filed on Mar. 13, 2001, entitled "Hydrogels That Undergo Volumetric Expansion In Response To Changes In Their Environment And Their Methods Of Manufacture And Use," and co-pending U.S. patent application Ser. No. 09/909,715 filed on Jul. 20, 2001, entitled "Aneurysm Treatment Devices and Methods of Use," each of which has been assigned to the assignee of the present application and which are incorporated by reference as if set forth herein in their entirety. Those skilled in the art will appreciate that the present invention may be manufactured with one or more of a variety of alternate reactive materials applied thereto, including, for example, collagen-polymer conjugate materials, photopolymerizable biodegradable materials, and other biodegradable cross-linked hydrogels known in the art.

Figure 1:
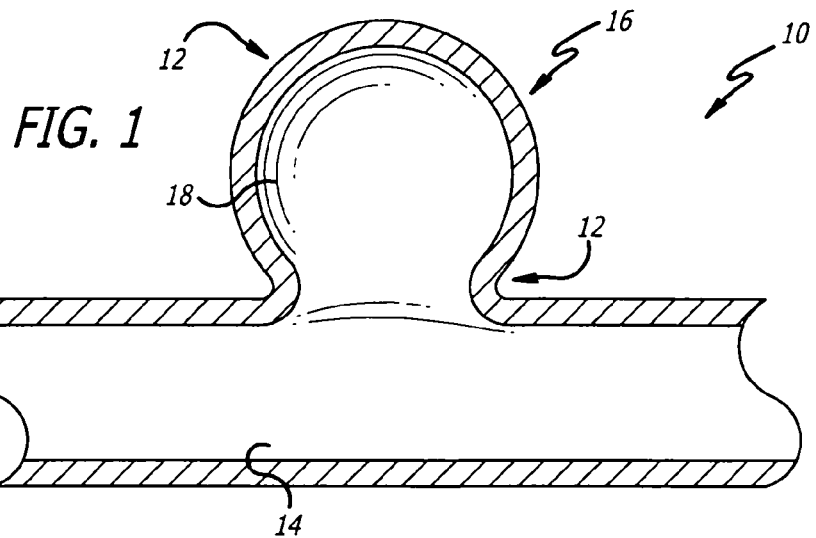
FIG. 1 shows a cross-sectional view of a blood vessel having a vascular aneurysm formed on its wall.

Aneurysms form as a result of outward pressure applied to a diseased or damaged blood vessel wall by blood flowing within the vessel, thereby resulting in a weakened section of tissue ballooning outwardly from a blood vessel. FIG. 1 shows an aneurysm 10 comprising a neck portion 12 in communication with a blood vessel 14 and having a dome portion 16 defining aneurysm cavity 18. Those skilled in the art will appreciate FIG. 1 illustrates an exemplary vascular aneurysm and is not intended to limit the scope or intent of the present invention.

Figure 2:
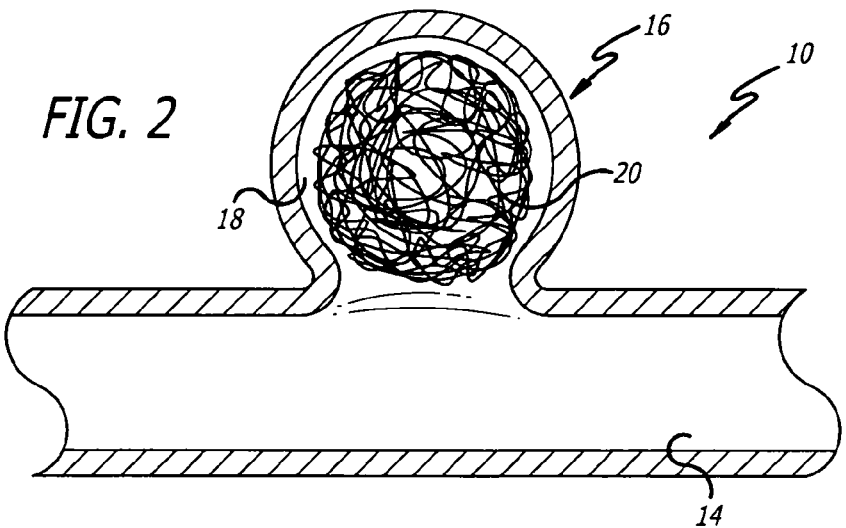
FIG. 2 shows a cross-sectional view of a prior art method of treating vascular aneurysm requiring the deposition of space-filling material within the vascular aneurysm.
Figure 3:
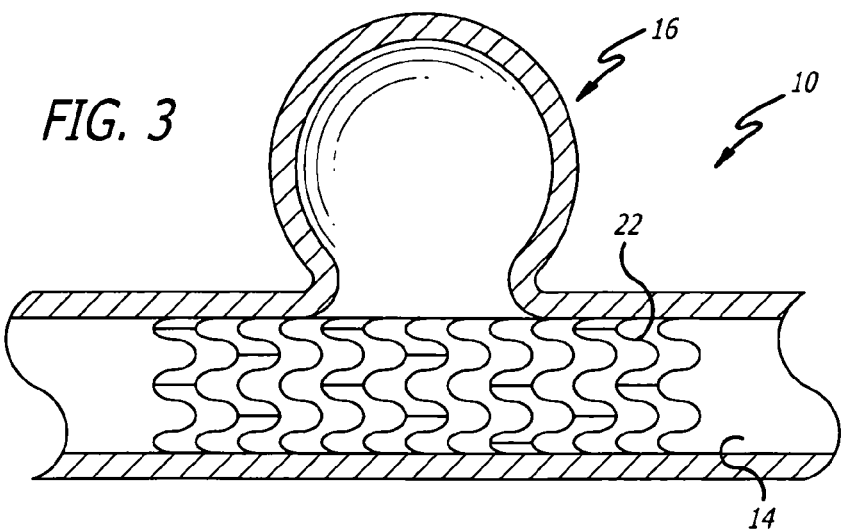
FIG. 3 shows a cross-sectional view of an alternate prior art method of treating vascular aneurysm wherein a mechanical stent is positioned near an aneurysm.

One method of treating an aneurysm requires the formation of an embolism proximate to or within the aneurysm, thereby restricting or depriving the aneurysm of blood flow and reducing the likelihood the aneurysm will rupture. FIGS. 2 and 3 show prior art devices used to repair aneurysms by artificially creating embolisms within or proximate to the aneurysm. In FIGS. 2 and 3 the reference numerals 10, 12, 14, 16, and 18 have analogous meanings to the reference numerals identifying the features of FIG. 1. FIG. 2 shows an aneurysm 10 in communication with a blood vessel 14. As shown, a vaso-occlusive device 20 is positioned within the aneurysm cavity 18. Typically, a micro-catheter or other device is used to inject or otherwise insert the vaso-occlusive device 20 into the aneurysm cavity 18, thereby decreasing the volume of the aneurysm capable of receiving blood from the blood vessel 14. FIG. 3 shows another device useful in treating aneurysms. As shown in FIG. 3, a stent 22 is positioned within a blood vessel 14 proximate to an aneurysm 10. A stent 22 is a mechanical scaffold used to provide support to otherwise incompetent or weakened tissue or to or maintain the patency of a narrowed or occluded blood vessel.

The present application discloses various embodiments of devices useful for the embolization or isolation of aneurysms. More particularly, the present application discloses various structures capable of implantation within an aneurysm or configured to be inserted into a blood vessel proximate to an aneurysm. Exemplary aneurysm treatment devices disclosed herein include, without limitation, neck bridges, vascular patches, stents, and intra-aneurysmal implants. In one embodiment, an aneurysm treatment device may include a series of interlocking or otherwise connected support members forming a predetermined shape. In an alternate embodiment, the aneurysm treatment device comprises an implant body which may be partially or completely inserted into an aneurysm formed on a blood vessel. The implant body may form a predetermined shape or, in the alternative, may form a random shape.

FIGS. 4 and 5a show cross sectional views of a portion of a support member 24 as used in the formation of a number of embodiments of the aneurysm treatment device of the present application before and following implantation. As shown in FIG. 4, the support member 24 may comprise a device substrate 26 having a reactive coating or covering or reactive material 28 applied to the exterior portion thereof prior to implantation. Once the material 28 has reacted it decreases the porosity of the support member 24 and thereby reduces the flow of blood through the walls of the device. The support member 24 having a non-reacted reactive coating or covering thereon has a first diameter of D. FIG. 5a shows reactive material 28 disposed on the support member 24 in a reacted state, wherein the reactive material 28 has expanded outwardly from the device substrate 26 in a preferential direction. As shown, in a reacted state the support member 24 assumes a second diameter of D', wherein the second diameter D' is larger than the first diameter D. The reactive material 28 may expand to increase the diameter of the support member 24 by between 10% and 200%. For example, in one embodiment the second diameter D' is about 20% larger than the first diameter D. In another embodiment the second diameter D' is at least about 25% larger than the first diameter D. Further, the reactive material 28 can expand in its reactive state to fill at least about 20% of the previously open area between adjacent support members 24. In the illustrated embodiment, the reactive material 28 has expanded more along the horizontal axis than the vertical axis. This permits the reactive material to inhibit flow outwardly through the device in the radial direction while minimizing its impact on longitudinal flow through the device and also minimizing the reactive material's impact on the overall profile of the device.

Figure 5C:
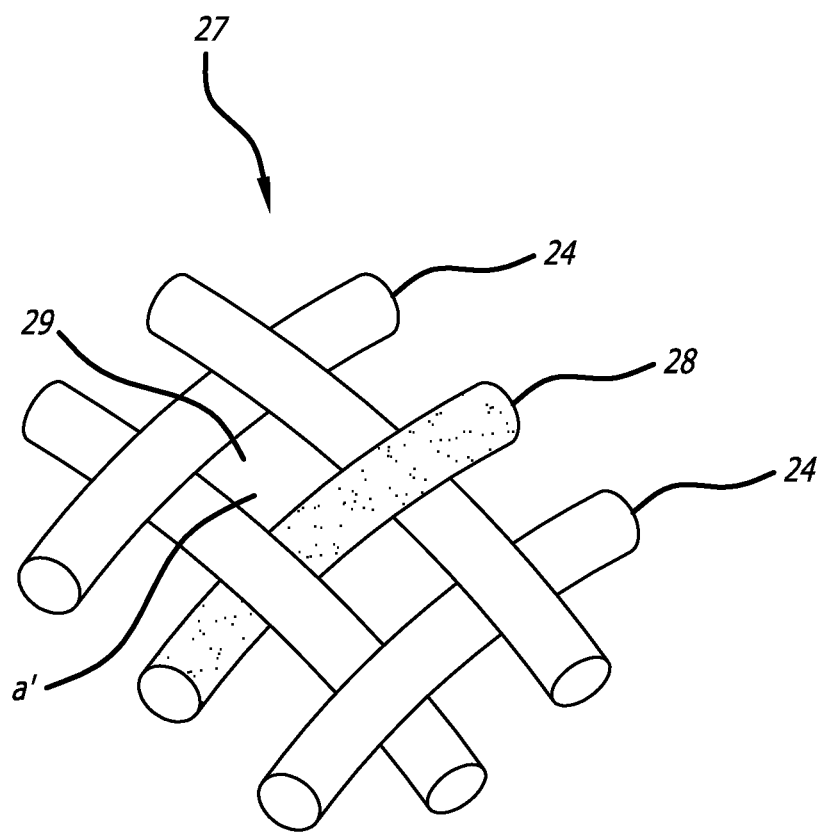
FIG. 5c shows a perspective view of an embodiment of an aneurysm treatment device comprising a structure having reactive material interwoven therein in a reacted state.

FIGS. 5b and 5c show an alternate embodiment of an aneurysm treatment device comprising a reactive material strand or wrap positioned on a support member 24. A number of support members 24 are interwoven thereby forming an interwoven structure 27. Reactive material or strands 28 may applied to a support member 24 or positioned within the interwoven structure 27 in a radial, axial, or radially and axial orientation. For example, a support member 24 may be wrapped with a reactive material strand 28. In an alternate embodiment, a reactive strand 28 may be disposed within the interwoven structure 27. Optionally, a reactive strand 28 may be interwoven within the structure 27. FIG. 5b shows an embodiment of the aneurysm treatment device with the reactive material 28 in a non-reacted state. As shown in FIG. 5b, the orifices 29 formed by the reactive material strand 28 and surrounding support members 24 have a first area of A. FIG. 5c shows the material strands 28 of the aneurysm treatment device in a reacted state wherein the orifices 29 formed by the reactive material strand 28 and surrounding support members 24 have a second area of A'. As shown, the second area A' of the orifices 29 in a reacted state is less than the first area A of the orifices in a non-reacted state, thereby limiting or inhibiting the flow therethrough. For example, the second area A' of the orifices 29 in a reacted state is at least about 20% less then the first area A of the orifices in a non-reacted state.

Referring again to FIGS. 4 and 5a, the reactive material 28 may have secondary operations performed on it, after it has been applied, to remove material in certain areas. In one embodiment, the reactive material may applied to the support members 24 in a substantially uniform thickness and then machined to remove some of the material from the inner and outer surfaces of the device to reduce the thickness of the reactive material 28 in those areas thereby reducing the overall radial thickness or profile of the device.

Additionally, the support members 24 of the various embodiments of the aneurysm treatment device may be manufactured from a plurality of biologically-compatible materials. For example, in one embodiment at least one support member 24 is manufactured from materials including, without limitation, platinum, gold, tantalum, titanium, stainless steel, tungsten, Nitinol, shape memory alloys, formed reactive material, or other suitable material. Optionally, at least one support member 24 may be manufactured from a variety of biologically-compatible polymer materials, including, but not limited to, polyurethane, polyvinyl alcohol, polyester, polytetrafluoroethylene, silicone, acrylic, or similar polymeric materials. At least one support member 24 may incorporate radio-opaque or echogenic materials or agents, thereby enabling the surgeon to precisely position the device within an aneurysm, blood vessel, or other hollow organ.

At least one support member 24 used in forming an aneurysm treatment device includes at least one reactive material 28 applied thereto. The reactive material 28 may be applied in a variety of ways known in the art. For example, one or more support members 24 may be coated with a reactive material 28. In an alternate embodiment, one or more support members 24 may have a reactive material 28 selectively applied thereto. For example, a reactive material 28 may be wrapped around or adhesively bonded to a portion of a support member 24. FIGS. 5*d*-5*e* show various embodiments of an aneurysm treatment device having a reactive fiber strand 28 applied thereto. As shown, the aneurysm treatment device comprises a support member 24 defining an internal passage 25. A portion of the support member 24 includes a reactive fiber stand 28 encircling a portion of the support member 24. In one embodiment, the reactive fiber strand may be adhesively coupled to the support member 24. For example, a fiber substrate having an adhesive applied to one surface and a reactive material 28 applied thereto may be positioned on or selectively applied to one or more support members 24.

The support member 24 receiving the reactive material strand 28 may have a constant or variable diameter or tangential width. For example, FIGS. 5*f* and 5*g* show an embodiment of a support member 24' having a variable tangential width. Support member 24' may be fabricated, for example, with a reduced diameter or tangential width, so that placement of the reactive material strand 28 around the support member 24' results in support member 24' having a tangential thickness that is substantially the same as the other support members 24'. As such, the diameter of the support member 24' having the reactive material wrap 28 applied thereto is approximately equal to the diameter of surrounding support members 24. As a result, the diameter of the aneurysm treatment device in a non-reacted state remains substantially constant. Additionally, the density of the device is not substantially greater in the region where the reactive material strand 28 is applied until after expansion occurs. In one embodiment, the reactive material wrap 28 is closely wound about the support member 24' so that when expansion occurs, it maximizes the change in diameter, thereby obstructing more flow between support members. In an alternate embodiment, the reactive material wrap 28 may be intermittently applied to the support member 24'. Further, there may be gaps between the reactive material wrap 28 windings. The reactive material strand 28 may have a diameter that is between 10% and 200% of the largest thickness of the support member 24. The reactive material wrap 28 may be attached to itself, to the support member 24, or both using attachment means well known in the art of biomaterials assembly, such as heat, adhesives, and the like. The reactive material wrap may be made from any of the reactive materials disclosed herein and may also include a core member of non-expansible material.

Optionally, at least one support member 24 and\or the reactive material 28 applied to the support member 24 may include one or more therapeutic agents applied thereto. Exemplary therapeutic agents include, for example, embolizing factors, anti-embolizing factors, and anti-restenotic compounds. For example, the reactive material 28 applied to one or more support members 24 may be chemically doped or impregnated with a drug, compound, bioactive agent and/or cellular material to promote endothelial cellular adhesion. A portion of the support member 24 or a portion of the reactive material 28 may be coated or modified to incorporate elements that promote the adhesion of beneficial cells or growth factors. An exemplary material is described in US Patent Application Publication Number 2002/0049495 to Kutryk et al. which is incorporated in its entirety by this reference. In an alternate embodiment, the reactive material 28 applied to one or more support members 24 may be chemically doped or impregnated with a drug or compound to promote tissue growth or impart other therapeutic benefit about the support member 24.

The reactive material 28 may be fabricated from a plurality of materials capable of expanding or volumetrically changing over time within the presence of blood or other fluid. For example, the Applicant's co-pending U.S. patent application Ser. No. 09/804,935 filed on Mar. 13, 2001 entitled "Hydrogels That Undergo Volumetric Expansion In Response To Changes In Their Environment And Their Methods Of Manufacture And Use" discloses a hydrogel useful as a reactive coating or covering or reactive material 28 for treating aneurysms. The above-referenced hydrogel comprises 1.25 g (0.021 moles) acrylamide, 0.87 g (0.009 moles) sodium acrylate, 0.005 g (0.00003 moles) N,N-methylenebisacrylamide, 7.95 g water, and 4.5 g sodium chloride (<10 micron particle size) added to an amber jar. The initiators, 53 microliters of N,N,N',N-tetramethylethylenediamine and 65 microliters of 20% w/w ammonium persulfate in water, are added and the solution is aspirated into a 3-cc syringe. The solution is then injected into 0.025" ID tubing and allowed to polymerize for 2 hours. The tubing is cut into 2-inch sections and dried in a vacuum oven. The dried hydrogel is washed 3 times in distilled water for 10-12 hours, 2 hours, and two hours, respectively, to remove porosigen, any unreacted monomer and any unincorporated monomers. The hydrogel may then be cut into sections of approximately 0.100 inch length called "pellets" and skewered with a platinum coil/wire assembly. In the alternative, the hydrogel may be drawn or formed into fibrous strands or portions of similar size and dimension as the support members 24. These pellets or strands are then hydrated in alcohol and dried under vacuum at approximately 55 C. for about 2 hours.

Thereafter, the dried pellets or strands are then placed in 50% hydrochloric acid/50% water and incubated for about 70 hours at 37 C. After the incubation, the excess hydrochloric acid solution is rinsed off of the pellets or strands with consecutive rinses of a) 70% isopropyl alcohol: 30% water for about 5 minutes, b) 100% isopropyl alcohol for about 15 minutes, c) 100% isopropyl for about 15 minutes and d) 100% isopropyl alcohol for about 15 minutes. The hydrogel pellets or strands are then dried under vacuum at 55 C. for at least 2 hours. Prior to or following the complete drying process, the pellets or strands may be selectively applied to the at least one support member 24 as desired in a plurality of ways. In one embodiment the reactive material 28 is applied to the entire surface of a support member 24. For example, the reactive material 28 may be maintained in a liquid form and a support member 24 may be submerged therein, thereby coating or covering the entire surface of the support member 24. In an alternate embodiment, the reactive material 28 is selectively applied to a portion of the support member 24. For example, the reactive material 28 may be selectively applied to the portion of a support member 24 which will engage a wall of a blood vessel. Optionally, a strand of the reactive material 28 may be wound about or around a support member 24. In another embodiment, the reactive material 28 may be applied to a substrate having a biologically compatible adhesive applied thereto. Thereafter, the substrate may be adhered to a support member 24 thereby applying the reactive material 28 thereto.

Once implanted in vivo, the reactive material 28 of the present embodiment becomes fully swollen within approximately one hour at physiological pH (about 7.4). For example, in one embodiment the reactive material 28 positioned on the support member 24 from a diameter of about 0.026 inch to a diameter of about 0.035 inch. As such, the cross sectional diameter of the support member 24 having reacted reactive material 28 thereon is about 25% larger than the cross sectional diameter of the support member 24 having non-reacted reactive material 28 thereon. Alternatively, the strands of reactive material 28 may be woven or integrated into the support structure. Optionally, the support structure 24 may be manufactured from a reactive material 28 without a substrate 26. (See FIG. 4)

FIGS. 6-9 show an embodiment of an aneurysm treatment device useful in isolating an aneurysm from a blood vessel. As shown in FIG. 6, the aneurysm treatment device comprises a vascular patch device 30 having a body member 32 formed by a plurality of interwoven or otherwise joined support members 24 axially displaced in relation to each other and capable of supporting weakened vascular tissue. The interwoven support members 24 form a plurality of fenestrations 34. In FIGS. 6-8, a reactive material 35 is selectively applied to the interwoven support members 24. As illustrated, the present embodiment permits the isolation and embolization of an aneurysm formed on a blood vessel without substantially occluding blood flow therethrough. As shown in FIG. 7, the vascular patch device 30 is formed by the plurality of support members 24 and may have an arcuate profile 36. In one embodiment, the arcuate profile 36 may be selected to approximate the radius of curvature of the receiving blood vessel, thereby further limiting blood vessel occlusion following implantation. The vascular patch device 30 may be manufactured in a variety of sizes, lengths, and radiuses. For example, the vascular patch device 30 may approximate 270 degrees of the receiving blood vessel, thereby using mechanical force to secure the device within the blood vessel. If desired, the vascular patch device 30 may incorporate malleable support members 24, thereby permitting the surgeon to adjust the arcuate profile 36 to conform to the radius of curvature of the receiving blood vessel during implantation.

Referring to FIG. 8, a vascular patch device 30 is shown positioned within a blood vessel 14 proximate to an aneurysm 10, wherein the device 30 traverses the opening 38 to the aneurysm cavity 18 formed by the neck portion 12. As shown, the expansion of the reactive material 35 results in a decrease in the size of the fenestrations 34 formed in the vascular patch device 30, thereby reducing the amount of blood entering the aneurysm. In an alternate embodiment, the device 30 may include a plurality of attachment devices (not shown) to assist in implanting and securing the device within a blood vessel. The attachment devices may include, for example, hooks, barbs, or similar devices manufactured from a plurality of materials, such as platinum, gold, tantalum, titanium, stainless steel, Nitinol, or other suitable material. In an alternate embodiment, the vascular patch device 30 may incorporate alternate attachment mechanisms, including, without limitation, adhesive materials, mechanical attachment mechanisms, or vacuum attachment mechanisms. FIG. 9 shows a cross sectional view of a blood vessel 14 having the vascular patch device 30 positioned proximate to an aneurysm 10. Those skilled in the will appreciate the present embodiment may be manufactured in a plurality of sizes, thereby enabling usage in various blood vessels to repair a plurality of aneurysms.

FIGS. 10-12 show an alternate embodiment of an aneurysm treatment device useful in treating aneurysms. As shown in FIG. 10, the aneurysm treatment device includes a resilient coiled bridge device 40 having a sinusoidal body member 42 defining a plurality of openings 44. The body member 42 may be formed along an arc 46, thereby aiding in the implantation of the device while limiting the occlusion of blood vessel. The resilient body member 42 may be compressed along the line 48 to enable delivery and positioning of the coiled bridge device 40 in vivo. Upon placement of the coiled bridge device 40 the resiliency of body member 42 exerts an outward pressure along line 50, wherein the resilient body member 42 engages the blood vessel wall (not shown). In an alternate embodiment, the coiled bridge device 40 may be used to provide mechanical support to weakened vascular tissue. As shown in FIG. 10, the body member 42 is coated with or otherwise disposes a reactive material, thereby increasing the resistance to the flow of blood to the aneurysm. FIG. 11 shows an alternate embodiment of the coiled bridge device 40 comprising a resilient sinusoidal body member 42 having at least one reactive section 52 disposed thereon, and defining a plurality of openings 44. The reactive portions 52 are areas selectively coated or otherwise incorporating a reactive material as defined above. The present embodiment permits the embolization of the aneurysm while limiting the occlusion within the blood vessel. FIG. 12 shows a cross sectional view of an aneurysm treatment device positioned within a blood vessel 14 wherein the at least one reactive section 52 occludes or inhibits blood flow to an aneurysm 10.

FIGS. 13-15 show yet another embodiment of an aneurysm treatment device useful in treating aneurysms formed on weakened vascular tissue. FIGS. 13-15 show various implantable expandable intraluminal prosthetic devices commonly referred to as "stents" capable of embolizing or isolating an aneurysm formed on weakened blood vessel tissue. In an alternate embodiment, the intraluminal vascular prosthetic devices may be used to provide mechanical support to weakened vascular tissue. As shown in FIG. 13, a helical expandable stent 54 comprises a cylindrical body member 60 disposed between a first end 56 and a second end 58. The cylindrical body member 60 defines a central lumen 62 co-axially aligned with the longitudinal axis 64 of the stent 54. The helical expandable stent 54 has a first diameter, D, thereby enabling insertion and positioning of the device within a blood vessel, and a larger second diameter, D', which is capable of engaging and supporting a blood vessel wall. As shown, a reactive material 66 is selectively applied to the external surface of the helical expandable stent 54. FIG. 14 shows an alternate embodiment of the helical expandable stent 54, comprising a cylindrical body member 60 having a first end 56 and a second end 58. The cylindrical body member 60 further comprises at least one reactive section 66 disposed thereon, thereby enabling the embolization or isolation of an aneurysm while limiting blood vessel occlusion. FIG. 15 shows cross sectional view of the present embodiment positioned within a blood vessel 14, wherein the at least one reactive section 66 occludes or otherwise inhibits blood flow to an aneurysm 10.

Figure 18:
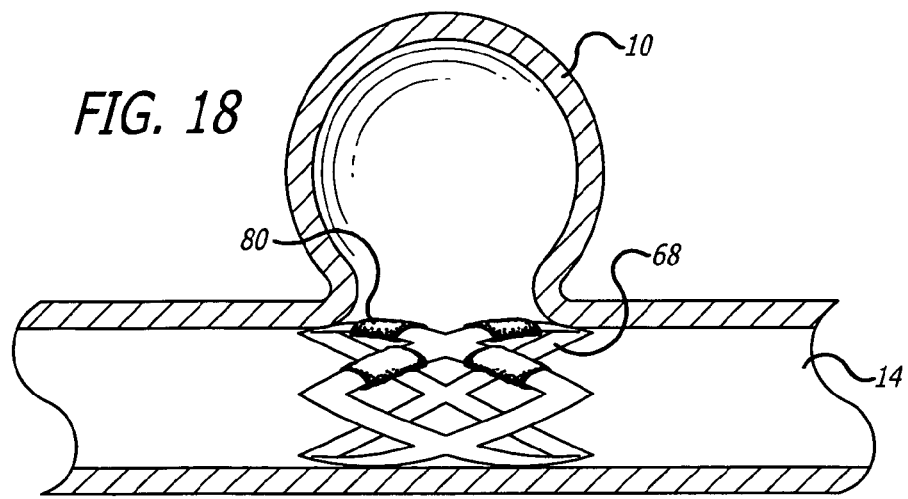
FIG. 18 shows a cross-sectional view of an embodiment of an aneurysm treatment device comprising a reticulated support device positioned within a blood vessel proximate a vascular aneurysm.

In another embodiment, FIGS. 16-18 show various embodiments of reticulated expandable intraluminal stents. As shown in FIGS. 16 and 17, the reticulated stent 68 comprises a first end 70 and a second end 72, having a cylindrical reticulated body 74 positioned therebewteen. The cylindrical reticulated body 74, which is comprised of a series of interconnected support members 24, defines a flow lumen 76 co-axially aligned along the longitudinal axis 78 of the stent 68 having a first compacted diameter D, and a second larger diameter D'. As shown in FIGS. 16-18, a reactive material may be applied to the external portion of the stent 68. Alternatively, the reactive material may be applied to selected areas or individual support members 24 may be manufactured from reactive material or otherwise incorporated therein. FIG. 18 shows an embodiment of the reticulated expandable stent 68 positioned within a blood vessel 14, wherein a reactive section 80 is increasing the resistance to the flow of blood to an aneurysm 10.

Figure 19:
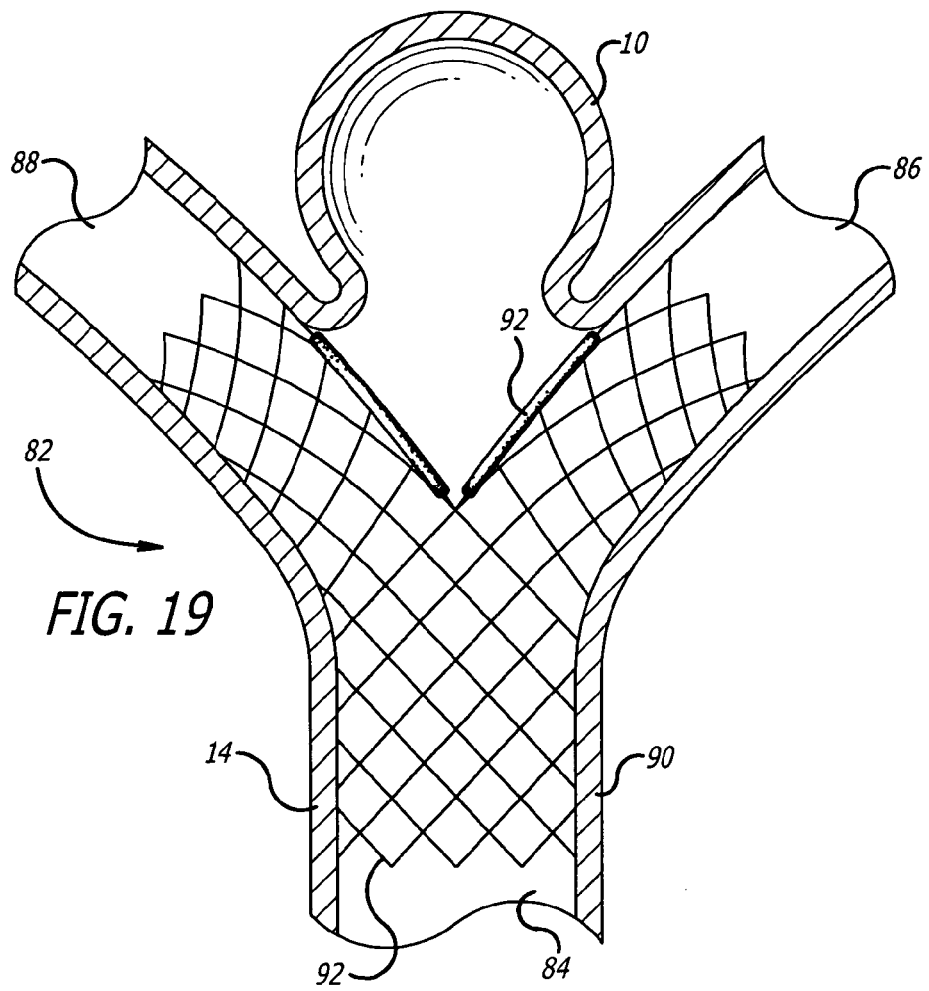
FIG. 19 shows a cross-sectional view of an embodiment of an aneurysm treatment device comprising a bifurcated stent device positioned within a blood vessel proximate to a vascular aneurysm.

FIG. 19 show an embodiment of an occlusive bifurcated supports. As shown in FIG. 19, the occlusive bifurcated support 82 comprising a first end 84, a second end 86, and a third end 88 and having a cylindrical body 90 positioned between the first, second, and third ends, 84, 86, and 88, respectively. The cylindrical body 90 further defines an internal lumen 92, which is in communication with the first, second, and third ends, 84, 86, and 88, respectively. The occlusive bifurcated support 82 has first diameter D, thereby enabling insertion and positioning of the device within a blood vessel, and a larger second diameter D', which is capable of engaging a blood vessel wall. As such, the cylindrical body 90 may be manufactured from a plurality of interlocking or otherwise joined support members 24, and may be reticulated. Reactive material 92 is incorporated into the cylindrical body 82, thereby occluding the aneurysm 10 formed on the blood vessel 14.

Figure 20:
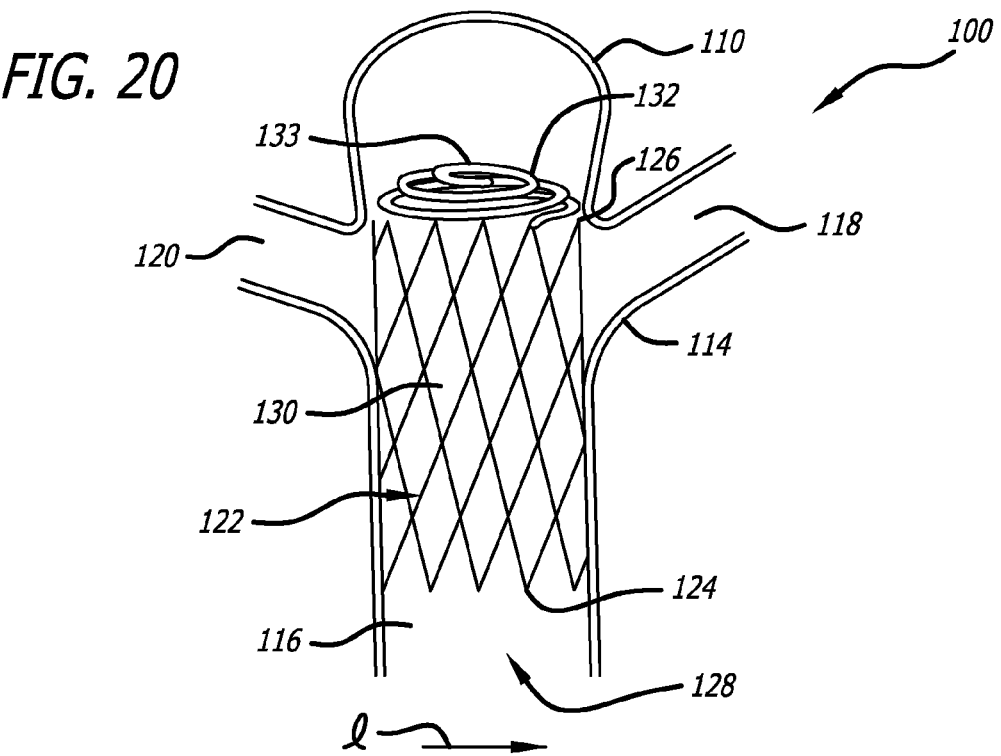
FIG. 20 shows a sectional view of an embodiment of an aneurysm treatment device comprising an occlusive support positioned within a blood vessel proximate to a vascular aneurysm.
Figure 21:
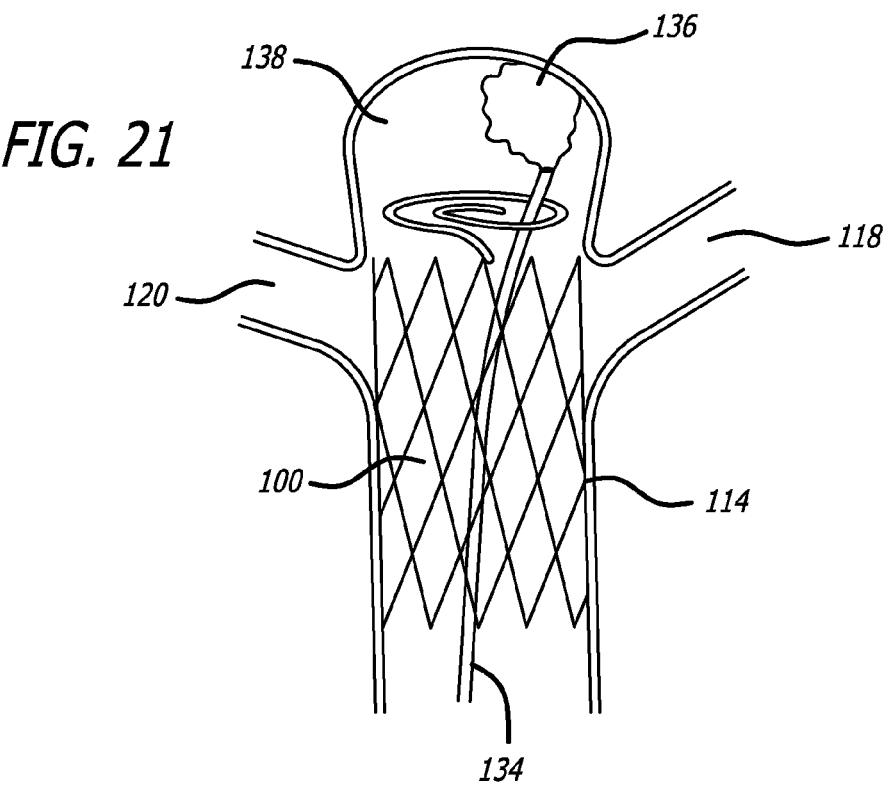
FIG. 21 shows a sectional view of an embodiment of an aneurysm treatment device having a catheter delivering a space occupying material to a vascular aneurysm through an occlusive support positioned within a blood.

FIGS. 20 and 21 show an embodiment of an occlusive support device. As shown in FIG. 20, an aneurysm 110 may form on a blood vessel 114 at a vascular junction. As discussed previously the aneurysm 110 may comprise a narrow neck portion 112 which is in communication with the blood vessel 114. The blood vessel 114 includes a first passage 116, a second passage 118, and a third passage 120. The occlusive support device 100 comprises one or more support members 122 forming a first end 124 and a second end 126 and defining a lumen 128 therethrough. One or more fenestrations 130 may be defined by the one or more support members 122. When implanted the one or more support members 122 provide support along line L to the surrounding tissue while permitting blood to flow through the fenestrations 130 formed by the support members 122. An end cap may be secured to the second end 126 of the occlusive support device 100 to inhibit flow into the aneurysm 110. The end cap 132 may be comprised from one or more filamentary elements that can easily be linearized for movement through a catheter. In one embodiment the end cap 132 is comprised of one of the support members 122 having reactive material 133 applied thereto. For example, as shown in FIGS. 20 and 21, the end cap 132 comprises a support member 122 formed in a circular shape of decreasing diameter 153. The end cap 132 may be substantially perpendicular to the longitudinal axis of the support device 100. Alternatively, the end cap 132 may have a convex or concave shape but otherwise positioned to be generally perpendicular to the longitudinal axis of the support device 100.

In some embodiments, the end cap 132 is designed to bridge the neck 112 of aneurysm 110 while minimizing its extension along the length of the support device 100 into either the aneurysm 110 or into passages 118 or 120 of blood vessel 114. To that end, as shown in FIGS. 20 and 21, the end cap 132 may have a diameter that approximates the size of the aneurysm neck 112 but will also have a relatively short extension along the longitudinal axis of the device compared to the length of the support device 100 so as to extend minimally into aneurysm 110 or flow passages 118 or 120. In one embodiment the end cap may have an extension along the longitudinal axis of the device that is less than two times its diameter. In another embodiment the extension of the end cap along the longitudinal axis of the device is less than its diameter.

In an alternate embodiment, the end cap 132 may be comprised of a plurality of interwoven support members 122 thereby forming a fenestrated end cap. Optionally, the end cap 132 is comprised of reactive material 133. As such, the end cap 132 may have no reactive material thereon, reactive material 133 applied thereto, or manufactured solely from one or more reactive materials 133. The diameter of the filamentary elements of end cap 132 can be made to be thinner than support members 122 so that when reactive material 133 is included the overall diameter of the filamentary elements of end cap 132 can be made to be less than the overall diameter of the support device. Once implanted, the end cap 132 decreases the flow of blood from the first passage 116 of the blood vessel into aneurysm 110 formed at the vascular junction, thereby directing the blood flow into the second and third passages 118, 120. As shown in FIG. 21, a space-occupying material 136 may be injected into the aneurysmal space 138 formed in the aneurysm 110. For example, a catheter 134 may be advanced though occlusive device 100 positioned within a blood vessel 114 and inserted through the end cap 132 into the aneurysmal space 138. Thereafter, a space occupying material 136 may be injecting or inserted into the aneurysmal space 138 from the catheter 134. Exemplary space occupying material 136 include, without limitation, hydrogels, hog hair, microfibrillar collagen, various polymeric agents, material suspensions, metallic or radio-opaque materials, and other space filling materials. In an alternate embodiment, therapeutic agents may be delivered to the aneurysmal space 138 through the catheter 134. Once the space occupying material 136 has been inserted into the aneurysmal space 138 the end cap 132 may be used to maintain the space occupying material 136 within the aneurysm 110 or to facilitate the formation of a substantially continuous surface bridging the neck of the aneurysm 110.

Figure 22:
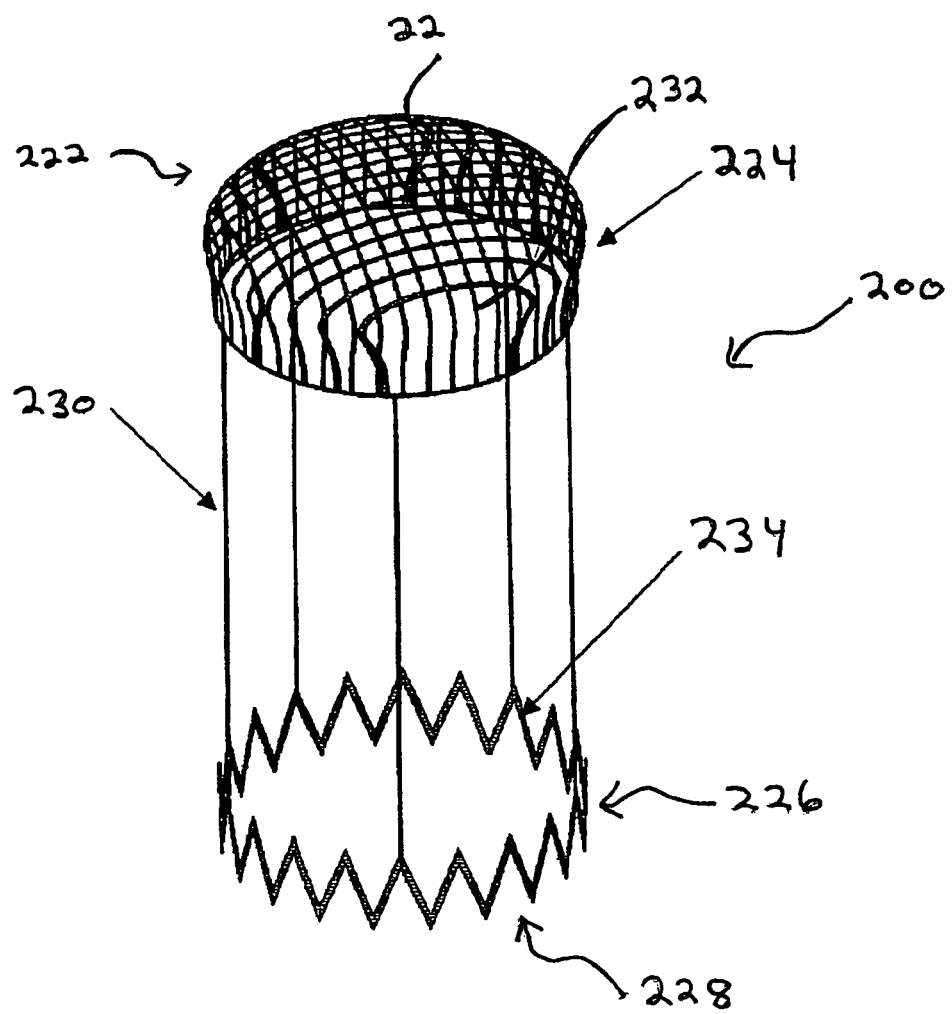
FIG. 22 shows a perspective view of an embodiment of an aneurysm treatment device having an occlusive member at a first end portion and an anchoring member at a second end portion, and a plurality of elongated members connecting the occlusive member to the anchoring member.
Figure 23:
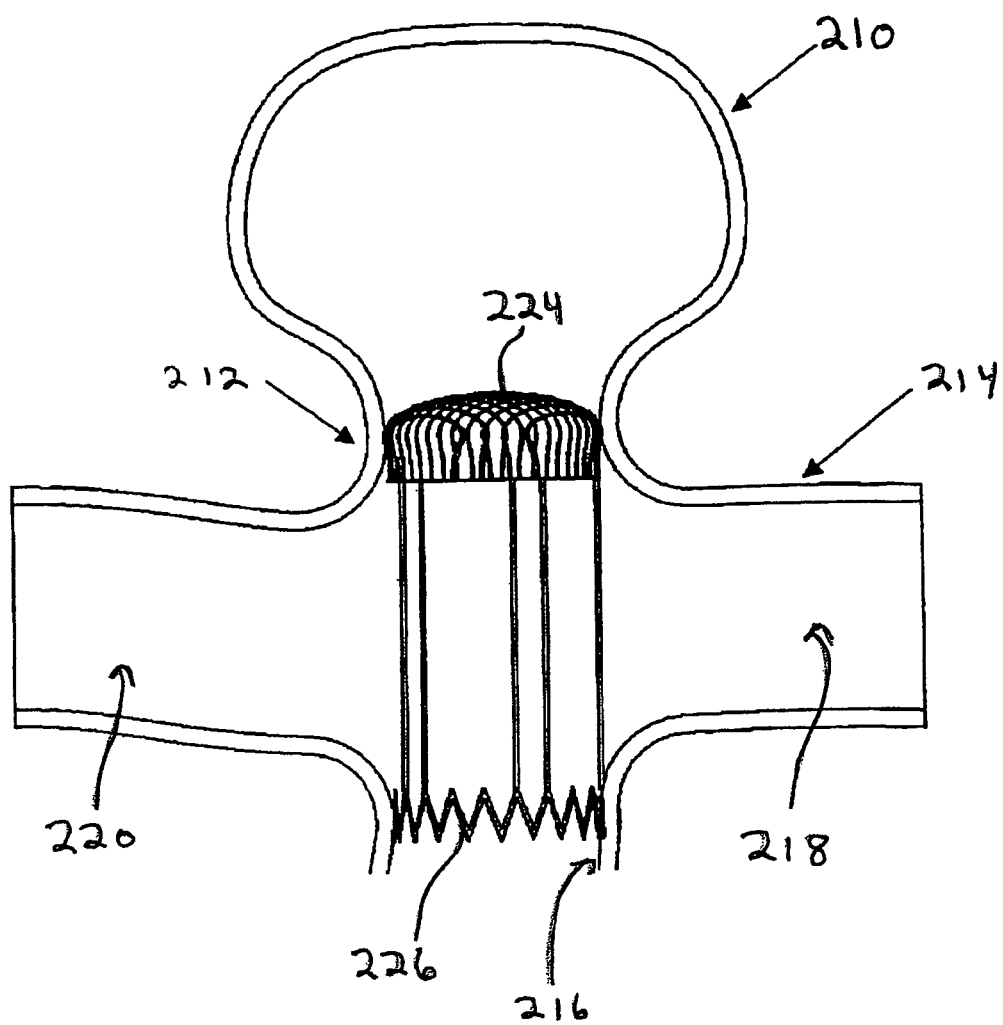
FIG. 23 shows a sectional view of the embodiment of FIG. 22 positioned within a blood vessel proximate to a vascular aneurysm.

FIGS. 22 and 23 show another embodiment of an occlusive support device 200. As with the embodiment of FIGS. 20 and 21, device 200 is particularly applicable for use with aneurysms formed at a vascular junction. Occlusive support device 200 is particularly useful in cases where coils or other embolic materials are being used to fill the aneurysm. Device 200 is structured so that is can be utilized to block the neck of the aneurysm to prevent the coils from migrating into the parent artery. As shown in FIG. 22, occlusive support device 200 comprises a first end portion or end cap 222 capable of preventing the migration of coils or, in the alternative, of partially occluding the neck 212 of the aneurysm 210. In the illustrated embodiment, end cap 222 comprises mesh 224. In alternate embodiments, end portion 222 could comprise a screen or plurality of wires or other structure capable of preventing migration of coils. The device 200 has an anchoring member 226 at a second end portion 228. The mesh 224 a is connected to the anchoring member 228 by elongated members 230. While elongate members 230 are shown substantially straight, they may have a number of bends or portions with a serpentine or sinusoidal shape to enhance the flexibility of the device. Further, the elongate members 230 may have a coil-like structure for even greater flexibility. As with the embodiment of FIGS. 20 and 21, the end cap 222 is designed to bridge the neck 212 of aneurysm 210 while minimizing its extension along the longitudinal axis of the device into either the aneurysm 210 or into passages 218 or 220 of blood vessel 214. Consequently, as shown in FIG. 23, the end cap or mesh 224 may have a diameter that approximates the size of the aneurysm neck 212 but will also have a relatively short extension along the longitudinal axis of the device compared to the length of the elongated members 230 so as to extend minimally into aneurysm 210 or flow passages 218 or 220. In one embodiment the end cap may have an extension along the longitudinal axis of the device that is less than two times its diameter. In another embodiment the extension of the end cap along the longitudinal axis of the device is less than its diameter.

Mesh 222 may be made from a variety of components such as metallic or fibrous wire, polymer thread or sheet, or cloth. The porosity of mesh 224 can be adjusted, depending on the application, from a few strands of wire to a non-porous plastic barrier. The elongated members 230 can be made from polymer or metallic wire, thread, or cut from a hypotube of polymer of metal. The elongated members 230 may be thin so as to minimize the interruption or blocking of blood flow into other blood vessels. The elongate members 230 are typically flexible to allow them to bend through tortuous anatomy. The anchoring member 226 may comprise a stent or other ring or sinusoidal member capable of supporting the vessel. The anchoring member 226 may have a variety of cell and strut patterns and may be either self-expanding or balloon expandable. Anchoring member 226 may be comprised of Nitinol, steel, titanium, chromium cobalt, Elgiloy, platinum or tantalum. Mesh 224 and anchoring members 228 may be comprised of polyurethane, PET (Dacron), nylon, polypropylene, Teflon, or other biocompatible polymers.

In one embodiment, device 200 is self-expanding. The self-expanding property can be due to elasticity or shape memory. Shape memory devices can be made from a variety of shape memory materials including nickel-titanium alloys, commonly known as Nitinol. Elastic devices can be made using a variety of materials including stainless steels, Elgiloy, titanium, nickel-titanium alloys and cobalt-chrome alloys. The mesh 224 is comprised of fine wires 232 of the same self-expanding material, the wires 232 having a diameter of approximately between 0.0005 to 0.005 inches. In one alternative, the mesh wires 232 may be laser cut from a thin sheet of the self-expanding material. The elongate members 230 may be made from the same self-expanding material as mesh 224 and may comprise wires of the same size as the mesh wires 232. Elongate members 230 could be extensions of mesh wires 232 or, in the alternative, they could be separate members which are attached to mesh 224 by, for example, welding, mechanical bonding, or in other ways known to those of skill in the art. Elongate members 230 may be initially straight or shaped into a particular pattern, such as a zig-zag pattern, along their length in order to enhance their flexibility.

Anchoring member 226 may be a self-expanding stent 234 which is formed from the same self-expanding material as mesh 224 and elongated members 230. The stent 234 may be made from wire, a rolled sheet, cut from a hypotube or made in a fashion known to those of skill in the art in stent fabrication. Elongated members 230 may be an extension of the stent pattern or, in the alternative, may be attached to the stent by, for example, welding, mechanical bonding, or in other ways known to those of skill in the art.

The entire assembly of the device 200 could be collapsed into a sheath or tubular catheter (not shown) having an inner member capable of carrying a guide wire. The inner member could also incorporate a restraining element such as a metal holder to grip the stent 234 until the sheath is withdrawn using techniques that are known to those of skill in the art. This would permit the mesh 224 and elongated members 230 to be partially deployed and, if necessary, re-sheathed during placement of device 200. The distal tip of the delivery sheath could be formed into what is known to those of skill in the art as a shepard's crook to allow the device to be deployed at a sidewall aneurysm. Radiopaque markers could be placed on either the device 200, the delivery device, or both, to aid in the visualization and placement of device 200.

In an alternative embodiment, device 200 can utilize a low-porosity barrier material, such as a polyethylene or PTFE sheet to form the mesh 224. The elongated members 230 could be formed of the same material. The elongated members 230 could thus be integral to mesh 224 or, in the alternative, could be attached to the mesh using heat, ultrasound, adhesive bonding, or in other ways known to those of skill in the art. In the alternative, the elongated members 230 could be metallic and could be attached to mesh 224 by mechanical bonding, by tying the elongated members 230 to mesh 224 using a thread or sutures, or in other ways known to those of skill in the art. Stent 234 could be a self-expanding metal with elongated members 230 attached thereto by mechanical bonding, sewing, welding, or in other ways known to those of skill in the art. Delivery and deployment of these variations would be the same or similar as described above, FIG. 23 shows support device 210 after deployment in a vessel 214. Aneurysm 210 is formed on blood vessel 214 at a vascular junction. Blood vessel 214 includes a first passage 216, a second passage 218, and a third passage 220. Device 210 is placed so that mesh 224 is proximal to the neck of aneurysm 210. The mesh 224 blocks the neck of aneurysm 210. Elongated members 230 connect mesh 224 to stent 234, which is deployed in the parent vessel 214 at some distance from aneurysm 210, thereby anchoring mesh 224 in position. Mesh 224 can be sized to approximate the size of the aneurysm neck, permitting the device to be placed at a vascular bifurcation or in complex vascular geometries. The size of elongated members 230 can be an order of magnitude smaller than the diameter of the branch vessels. Thus, even though elongated members 230 might cross the branch vessels they are unlikely to occlude them. Since the function of occluding the aneurysm 210 is performed by mesh 224, stent 234 can be relatively short and only needs to have relatively low radial strength. This greatly enhances the delivery accuracy of the device compared to a conventional stent. Furthermore, since the mesh 224 is closely sized to the aneurysm neck, its porosity can be adjusted by either material selection or the addition of expandable coatings or coverings which could obviate the need for placing coils in the aneurysm.

Device 210 may be deployed in a delivery catheter which is maneuvered to the aneurysm neck. Mesh 224 may be at the distal end of the catheter which is placed proximal to the aneurysm neck and a retaining sheath may be retracted, deploying the elongated members 226 and then deploying anchoring member 224 in the parent vessel.

In some embodiments, mesh 224 may be made to be sufficiently porous so that a micro catheter could be positioned at the aneurysm neck to deliver coils or other embolic materials into the aneurysm. Alternatively, a micro catheter may be placed in the aneurysm to deliver coils prior to placement of device 210. In yet another embodiment, mesh 224 has a porosity low enough so as to sufficiently occlude the aneurysm from blood flow without the need for coils.

In the above embodiments, mesh 224 could be coated with a reactive material, such as a hydrogel. In a device where mesh 224 is intended to provide low-porosity, this variation allows for the device 200 to be collapsed to a smaller size for delivery. Upon delivery of the device, as the hydrogel hydrates, the pores of mesh 224 would become smaller, providing greater occlusion of the aneurysm 210 or greater resistance to flow into aneurysm 210. In any embodiment, the presence of hydrogel at the neck of aneurysm 210 or 310 can promote a healing response from the body to help to permanently occlude the aneurysm 210 Or 310.

The devices disclosed in this application can be fabricated with a least a portion of their external surface having features that promote the adhesion or mechanical interlock of the reactive material. This can improve the durability of the reactive material. These surface features can be created by machining or chemical processing and a reactive material can be applied in a variety of ways as described in co-owned U.S. patent application Ser. No. 10/177,651, the disclosure of which is hereby incorporated by reference, as if fully set forth herein.

For example, The external surface of device 200 may have a topography characterized by surface features which deter longitudinal slippage of the application of reactive material over the outer surface and/or which result in some mechanical engagement or interlock between the reactive material and the device 200. In this regard, the outer surface of device 200 may have one or more cavities formed therein, at least some of those cavities having side walls which are disposed at angles of about 75 or more degrees relative to the longitudinal axis of the device 200 (or relative to the outer surface of the device 200 immediately adjacent to those side walls) and wherein at least a portion of the reactive material extends into at least some of the cavities so as to deter separation of the reactive material from the device 200.

In one particular embodiment of the surface modification, grooves or pores are created in the treatment device such that they have at least one surface that has an angle greater than about seventy five degrees to the exterior of the treatment device. FIG. 24 shows a substantially solid member 242 which has generally rectangular cavities in the nature of slots 246 formed inwardly from the outer surface 247 thereof. The reactive material 244 is disposed continuously over the outer surface 247 of the solid member 242. A longitudinal axis LA is projectable through the solid member 242. A wall axis WA is projectable along the side wall 248 of each slot 246. For at least some of the slots 246, the wall axis WA is substantially perpendicular to the longitudinal axis LA, such that angle A will be approximately 90 degrees, as shown in FIG. 24. It will be appreciated that, in some embodiments, the side walls 248 of at least some slots 246 may be slanted or angled such that the slot 246 is wider at its bottom B than at its top T, thereby creating an undercut which further mechanically locks or frictionally engages the reactive material 244 to the solid member 242. In some embodiments, grooves can be cut into the external surface of the device in, for example, a circular or helical pattern which is substantially perpendicular to the axis of the device.

FIGS. 25A-25D show, in step by step fashion, a method for manufacturing a device 262 having non-continuous, discrete deposits of a reactive material. In this method, a device 262 having a surface 263 is initially provided as shown in FIG. 25A. A plurality of cavities 266 such as blind bore holes, slots, indentations, depressions, cuts, grooves, etc. are formed in the outer surface 263 of the device 262. This may be accomplished by any technique known in the art such as mechanical drilling, boring, laser etching, cutting, EDM, photochemical etching, etc. As shown in FIG. 25B, wall axes WA projected parallel to at least portions of the sidewalls 265 of at least some of the cavities 266 preferably form an angle A relative to the longitudinal axis LA of the device 262 or a longitudinal axis of the outer surface 263 of device 262 are preferably greater than 75 degrees and more preferably greater than 90 degrees. In some embodiments, as shown in FIG. 25B (alt) the sidewalls 265A of the cavities 266A may be angled or curved such that the cavities 266A are wider at their bases B than at their tops T. This results in the formation of an angle A greater than 90 degrees and forms an undercut whereby the later-applied reactive material 264 (FIGS. 25C-25D) becomes mechanically or frictionally interlocked or engaged by the sidewalls 265A of the cavities 266A.

After the cavities 266 or 266A have been formed in the device 262, the reactive material 264 is deposited in the cavities 266 or 266A In some embodiments, such as the specific example shown in FIGS. 25C-25D, the reactive material 264 is a swellable or expandable coating or covering 264 which swells or expands after coming in contact with a body fluid BF such as blood or other liquid such as saline solution or sterile water. The reactive material 264 may be initially applied over the entire outer surface 266 of the working element 262 and the layer of reactive material deposited on the outer surface may then be wiped or scraped away, or otherwise removed, leaving discrete deposits of reactive material 264 within the cavities 266 such that the upper surface 264 of each mass of reactive material 264 is substantially flush with or even slightly below the level of the outer surface 266.

Thereafter, when the device 262 is immersed in blood or other body fluid BF or when it is immersed in of contacted by a liquid (saline, water, etc.), the deposits of reactive material 264 will expand or swells such that the upper surface US of each reactive material deposit 264 protrudes above the outer surface 266 of the working element 262. Alternatively, the reactive material may expand in response to changes in its environment, such as changes in physiological pH. In this manner, the expansion of the reactive material creates a non-continuous coating or covering system which comprises discrete raised knobs, bumps, ridges, etc. of reactive material 264, on the outer surface 266 of the working element 262. Such coating or covering 264 may impart lubricity or form a slippery substance which facilitates the desired insertion, positioning, movement and/or withdrawal of the device 262 from the body of a patient.

Referring again to FIG. 23, in a particular embodiment which utilizes a reactive material applied to mesh 222, the reactive material may have operations applied to it after it has been applied to remove materials in certain areas. For example, the reactive material may be applied to the wire mesh 224 in a substantially uniform thickness and thereafter machined to selectively remove material so that the pores of the mesh 224 are substantially filled with the reactive material once it hydrates without adding to the thickness of the mesh itself.

Figure 26:
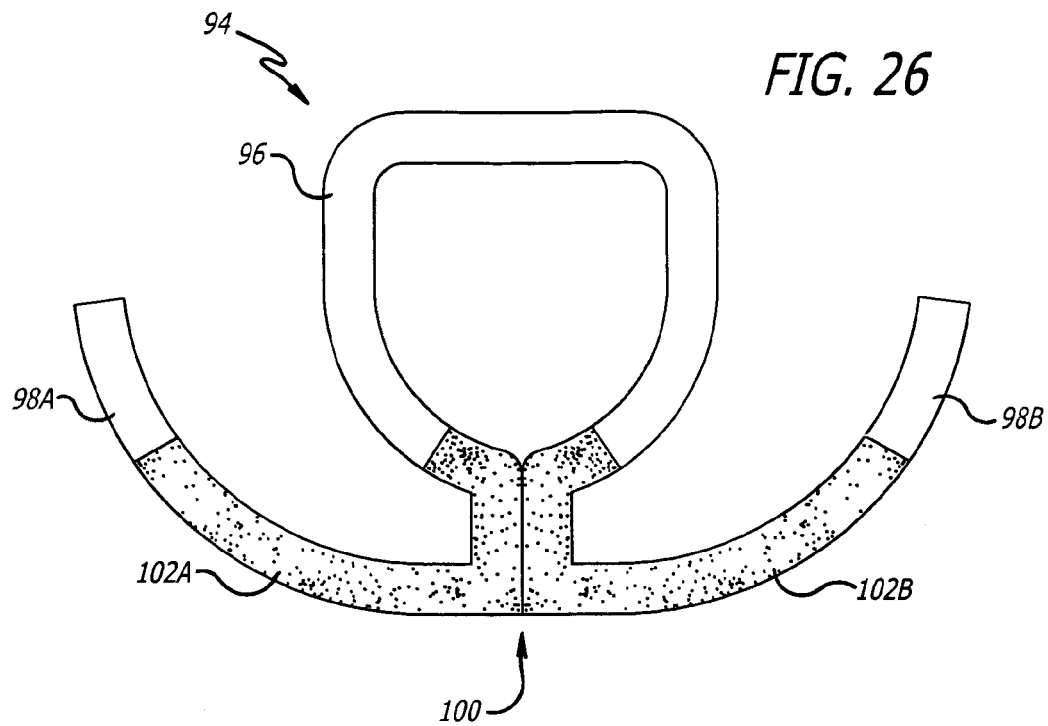
FIG. 26 shows a perspective view of an embodiment of an aneurysm treatment device comprising an intra-aneurysmal bridge device an aneurysm treatment device useful in restricting the flow of blood to a vascular aneurysm.
Figure 27:
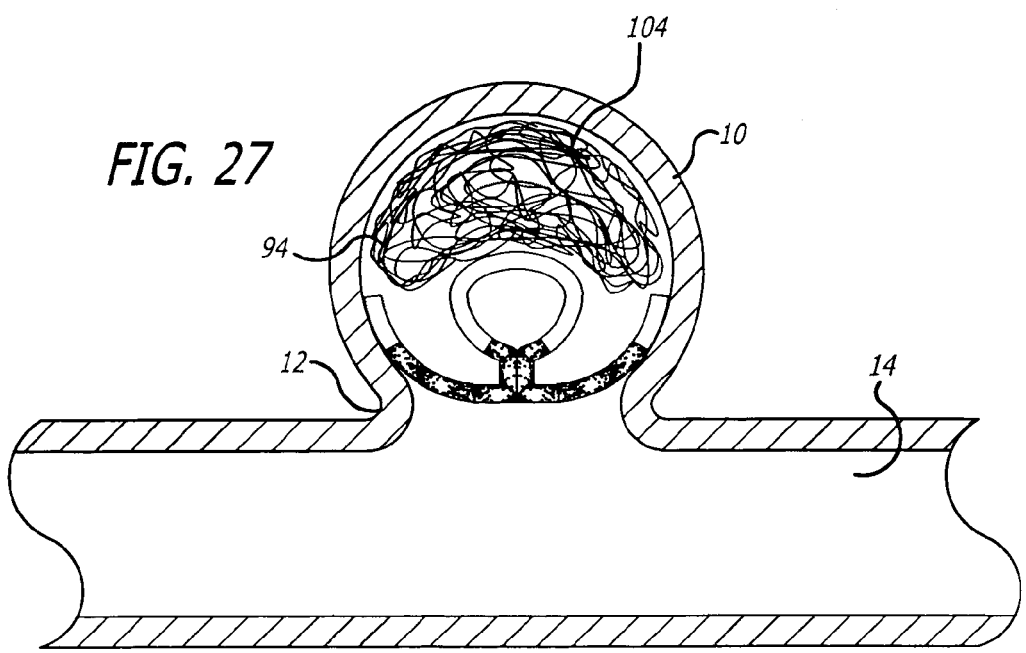
FIG. 27 shows a sectional view of an embodiment of the aneurysm treatment device shown in FIG. 26 positioned within a vascular aneurysm.

FIGS. 26 and 27 show an embodiment of an intra-aneurysmal neck bridge structure. As shown, the intra-aneurysmal neck bridge structure 150 comprises device body 152 in communication with at least two engagement members 154A and 154B cooperatively forming a device joint 156. In one embodiment, the device joint 156 sealably isolates the aneurysm from the flow of blood through the blood vessel. The engagement members 154A-B are formed to approximate the radius of curvature of the aneurysm thereby providing an interface between the device and the aneurysm. Reactive portions 158A-B are positioned on the engagement members 154A-B, respectively. As shown in FIG. 27, a reactive or occlusive material 160 may be inserted into the aneurysm 162 prior to or after applying the intra-aneurysmal neck bridge structure 150. Such reactive or occlusive materials 160 may include, for example, a plurality of materials such as hydrogels, hog hair, microfibrillar collagen, various polymeric agents, material suspensions, metallic or radio-opaque materials, and other space filling materials.

The present application further discloses methods of treating vascular aneurysms. In the one embodiment, a method of percutaneously inserting an aneurysmal treatment device into an aneurysm is disclosed and includes percutaneously inserting am aneurysmal treatment device into a blood vessel, advancing the treatment device to a location proximate to a vascular aneurysm, and applying the device to the aneurysm or surrounding tissue without substantially restricting blood flow through the blood vessel. The aneurysm treatment devices disclosed in the present application may be delivered to a situs in vivo in a plurality of manners, including, for example, on guidewires, balloon catheters or through micro-catheters. FIG. 28 shows an exemplary embodiment 170 of an aneurysm treatment device being applied to an aneurysm 172 using a balloon micro-catheter 174.

In practice, the surgeon positions an aneurysm treatment device, for example, an expandable reticulated stent 170 on a delivery device, for example, a micro-balloon catheter 174. Thereafter, a first incision is made proximate a blood vessel and a guidewire 176 is inserted therein. Commonly, the guidewire will enter the circulatory system through the femoral artery, the femoral vein, the jugular vein, the carotid artery, or a similar blood vessel. The guidewire 176 may then be directed through the circulatory system to a location proximate to the aneurysm 172 and, thereafter, made to exit the body through a remote exit point. The delivery device 174 and stent 170 may then be advanced along the guidewire 176 and positioned proximate to the aneurysm 172. Typically, visualization methods, such as fluoroscopy, ultrasound visualization, or echogenic location are utilized to precisely position the delivery device near or within the aneurysm 172. Once positioned, the micro-balloon 174 is inflated and the expandable reticulated stent 170 is applied to the tissue. The portion of the expandable reticulated stent 170 disposing the reactive material 178 is positioned proximate to the aneurysm. Thereafter, the delivery device 174 and guidewire 176 are removed from the body. The activation of the reactive material 178 selectively applied to the stent 170 increases the resistance to the flow of blood to the aneurysm 172. The activation process may result from a plurality of occurrences, including, for example, the presence of a physiological pH for an extended period, the presence of an enzyme or other material within the blood, electromagnetic-activation resulting from the introduction of a pre-determined wavelength of electromagnetic energy. The procedure above discloses one such activation method, however, other activation methods known in the art are contemplated.

Optionally, the method of treating an aneurysm may include an embolic material or one or more devices which may be inserted either prior to or after the deployment of the treatment device.

In closing it is understood that the embodiments of the aneurysm treatment device disclosed herein are illustrative of the principles of the invention. Other modifications may be employed which are within the scope of the invention. Accordingly, the present invention is not limited to that precisely as shown and described in the present invention.

What is clamed is:

1. An apparatus for treating vascular aneurysms, comprising:
    an occlusive support device comprising one or more support members forming a first end portion and a second end portion and defining a lumen therethrough; and
    a rounded end cover member forming a longitudinal sidewall at said first end portion of said occlusive support device;
    wherein said end cover member has openings and said end cover member comprises a reactive material that is configured to hydrate upon delivery of the device and to reduce the size of said openings;
    an anchoring member at said second end portion; and,
    a plurality of elongated members along said longitudinal axis and connecting said end cover member to said anchoring member, said elongated members having a length selected to span across a blood vessel adjacent to a targeted aneurysm to connect the anchoring member to the end cover while minimizing resistance to blood flow through the adjacent blood vessel.

2. The apparatus of claim 1 wherein said end cover member comprises at least one of said one or more support members.

3. The apparatus of claim 1 wherein said end cover member comprises a support member formed in a circular shape of decreasing diameter.

4. The apparatus of claim 1 wherein said end cover member comprises a plurality of interwoven support members forming a fenestrated end cover.

5. The apparatus of claim 1 wherein said reactive material is applied to said end cover member.

6. The apparatus of claim 1 wherein said end cover member comprises a porous material.

7. The apparatus of claim 1, wherein said end cover is capable of increasing the resistance of blood flow therethrough.

8. The apparatus of claim 1 wherein said end cover member comprises one or more filamentary elements.

9. The apparatus of claim 8 wherein said filamentary elements are arranged to form an end cover member selected from the group consisting of a coil, a weave, a braid, a mesh, a screen, and a cable.

10. The apparatus of claim 1 wherein said reactive material is a hydrogel.

11. The apparatus of claim 1 wherein said reactive material in configured to expand in response to changes in physiological pH.

12. The apparatus of claim 1 wherein said end cover member comprises a mesh member comprised of a plurality of wires.

13. The apparatus of claim 12 wherein said mesh member is comprised of fine, self-expanding wires.

14. The apparatus of claim 12 wherein said mesh member is a low porosity mesh member.

15. The apparatus of claim 14 wherein said low porosity member is a nonporous barrier.

16. The apparatus of claim 1 wherein said end cover has an extension along said longitudinal axis of said device that is less than said end cover diameter.

17. The apparatus of claim 1 wherein said end cover has an extension along said longitudinal axis of said device that is less than two times said end cover diameter.

18. The apparatus of claim 1, wherein said support device is substantially cylindrical and said support device comprises one or more support members along said longitudinal axis and defining fenestrations through said support device.

19. The apparatus of claim 18 wherein said end cover member comprises a plurality of said one or more support members interwoven together.

20. The apparatus of claim 1 wherein said anchoring member is a stent.

21. The apparatus of claim 20 wherein said stent is comprised of support members defining fenestrations through said support device.

22. The apparatus of claim 1 wherein said end cover member is comprised of self-expanding end cover member wires and said elongated members comprise the same self-expanding material as said end cover member and said elongated members comprise wires of the same size as said end cover member wires.

23. The apparatus of claim 22 wherein said elongated members are extensions of said end cover member wires.

24. The apparatus of claim 22 wherein said elongated members are attached to said end cover member.

25. The apparatus of claim 22 wherein said anchoring member is comprised of the same self-expanding material as said end cover member and said elongated members.

26. The apparatus of claim 22 wherein said elongated members are an extension of said anchoring member.

27. An apparatus for treating vascular aneurysms, comprising:
an occlusive support device comprising a longitudinal axis having first end portion and a second end portion;
a rounded end cover member forming a longitudinal sidewall at said first end portion of said occlusive support device, wherein said end cover member has an end cover diameter and said end cover is generally perpendicular to said longitudinal axis of said support device, wherein said end cover has an extension along said longitudinal axis of said device that is less than two times said end cover diameter and wherein said end cover member has openings and said end cover member comprises a reactive material that is configured to hydrate upon delivery of the device and to reduce the size of said openings; and
an anchoring member at said second end portion;
elongated members connecting the first end portion to the second end portion, said elongated members having a length selected to span across a blood vessel adjacent to a targeted aneurysm to connect the anchoring member to the end cover member while minimizing resistance to blood flow through the adjacent blood vessel.

28. The apparatus of claim 27 wherein said reactive material in configured to expand in response to changes in physiological pH.

29. An apparatus for treating vascular aneurysms, comprising:
an occlusive support device comprising one or more support members forming a first end portion and a second end portion and defining a lumen therethrough; and
a rounded mesh end cover member at said first end portion of said occlusive support device, said mesh end cover member comprised of at least one of said one or more support members, said rounded mesh end cover member forming a longitudinal sidewall;
wherein said end cover member has openings and said end cover member comprises a reactive material that is configured to hydrate upon delivery of the device and to reduce the size of said openings; and
an anchoring member at said second end portion;
elongated members connecting the first end portion to the second end portion, said elongated members having a length selected to span across a blood vessel adjacent to a targeted aneurysm to connect the anchoring member to the end cover while minimizing resistance to blood flow through the adjacent blood vessel.

30. The apparatus of claim 29 wherein said reactive material in configured to expand in response to changes in physiological pH.

* * * * *